US012740745B2

(12) United States Patent
Kulkarni et al.

(10) Patent No.: US 12,740,745 B2
(45) Date of Patent: Sep. 22, 2026

(54) WEARABLE ALCOHOL MONITORING DEVICE

(71) Applicant: ARBORSENSE, INC., Ann Arbor, MI (US)

(72) Inventors: Girish Kulkarni, Ann Arbor, MI (US); Don Kahaian, Farmington, MI (US); John Ross, Haslett, MI (US)

(73) Assignee: ARBORSENSE, INC., Ann Arbor, MI (US)

(*) Notice: Subject to any disclaimer, the term of this patent is extended or adjusted under 35 U.S.C. 154(b) by 218 days.

(21) Appl. No.: 18/835,203

(22) PCT Filed: Feb. 2, 2023

(86) PCT No.: PCT/US2023/012167
§ 371 (c)(1),
(2) Date: Aug. 1, 2024

(87) PCT Pub. No.: WO2023/150198
PCT Pub. Date: Aug. 10, 2023

(65) Prior Publication Data

US 2025/0160738 A1 May 22, 2025

Related U.S. Application Data

(60) Provisional application No. 63/305,811, filed on Feb. 2, 2022.

(51) Int. Cl.
*A61B 5/1477* (2006.01)
*A61B 5/00* (2006.01)

(52) U.S. Cl.
CPC .......... *A61B 5/4845* (2013.01); *A61B 5/1477* (2013.01); *A61B 5/681* (2013.01); *A61B 2560/0252* (2013.01); *A61B 2562/029* (2013.01)

(58) Field of Classification Search
CPC ..... A61B 5/4845; A61B 5/1477; A61B 5/681; A61B 2560/0252; A61B 2562/029; A61B 5/1455; G01N 33/98
See application file for complete search history.

(56) References Cited

U.S. PATENT DOCUMENTS 10,845,324 B2 11/2020 Kulkarni et al.
2008/0009693 A1* 1/2008 Hawthorne ........ A61B 5/14546 600/364

(Continued)

OTHER PUBLICATIONS

Hawthorne, J.S. et al., "Transdermal alcohol measurement: A review of the literature," Canadian Society of Forensic Science Journal 39.2 (2006), pp. 65-71.

(Continued)

*Primary Examiner* — Andrey Shostak
(74) *Attorney, Agent, or Firm* — Brooks Kushman P.C.

(57) ABSTRACT

A wrist-worn device includes a device housing, an electrochemical sensor, control circuitry, optional tamper sensors, and a water-absorbing material. The device housing includes an upper housing and a lower housing attached to the upper housing. The lower housing includes a top wall and a circumferential side wall. The top wall defines a first access opening. The device housing also includes a wrist piece having a first face and a second face that defines a trench in the first face that protrudes from the second face as a closed curve-shaped protrusion. The lower housing and the wrist piece cooperatively form an amplification chamber. The wrist piece also defines a plurality of vent holes that allow transdermally emitted ethanol to enter the amplification chamber. The control circuitry is configured to receive measurements and to calculate transdermal alcohol concentrations from the electrochemical sensor.

24 Claims, 35 Drawing Sheets

(56) References Cited

U.S. PATENT DOCUMENTS

| | | | | |
|---|---|---|---|---|
| 2008/0216561 | A1* | 9/2008 | Cooper | A61B 5/681 73/53.01 |
| 2014/0349256 | A1 | 11/2014 | Connor | |
| 2014/0365142 | A1 | 12/2014 | Baldwin | |
| 2014/0377877 | A1 | 12/2014 | Bürgi et al. | |
| 2015/0346197 | A1* | 12/2015 | Chen | A61B 5/4845 435/287.1 |
| 2020/0373598 | A1 | 11/2020 | Kulkarni et al. | |

OTHER PUBLICATIONS

International Search Report and Written Opinion dated Apr. 14, 2023 for PCT Appn. No. PCT/US2023/012167, 7 pgs.

* cited by examiner 26
78
37
37
78
34
33
76
74
74

26
32
78
38
76
28
76

100, 102 vent path

104

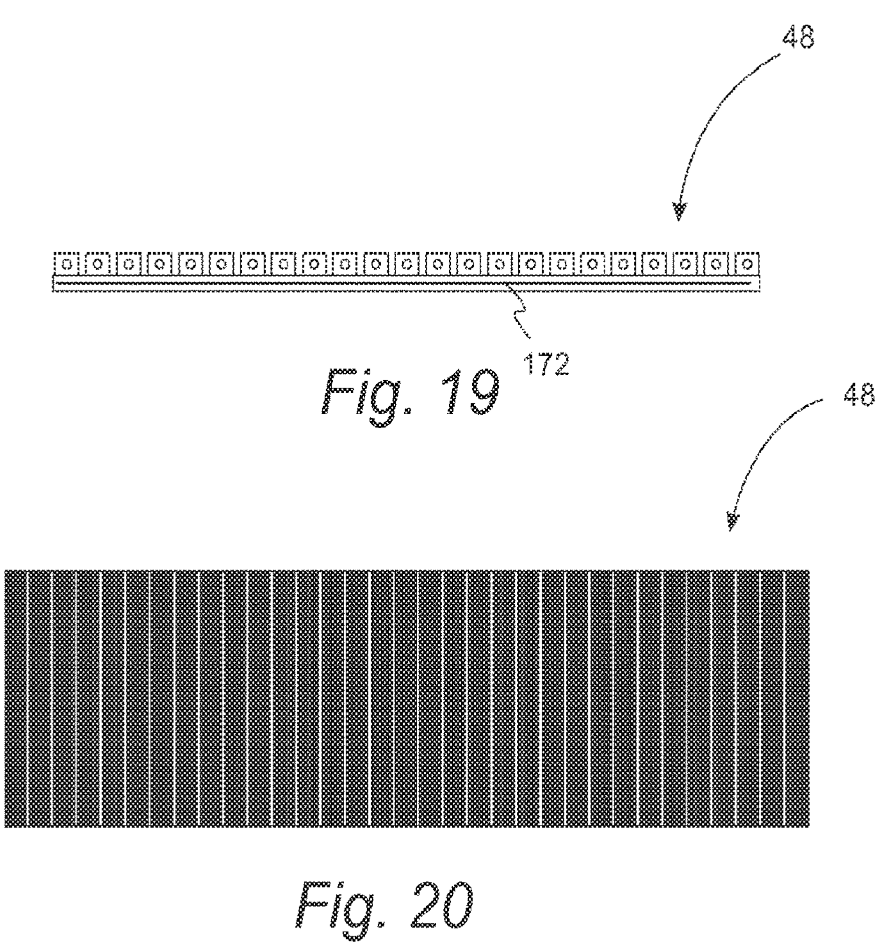
Fig. 19
Fig. 20
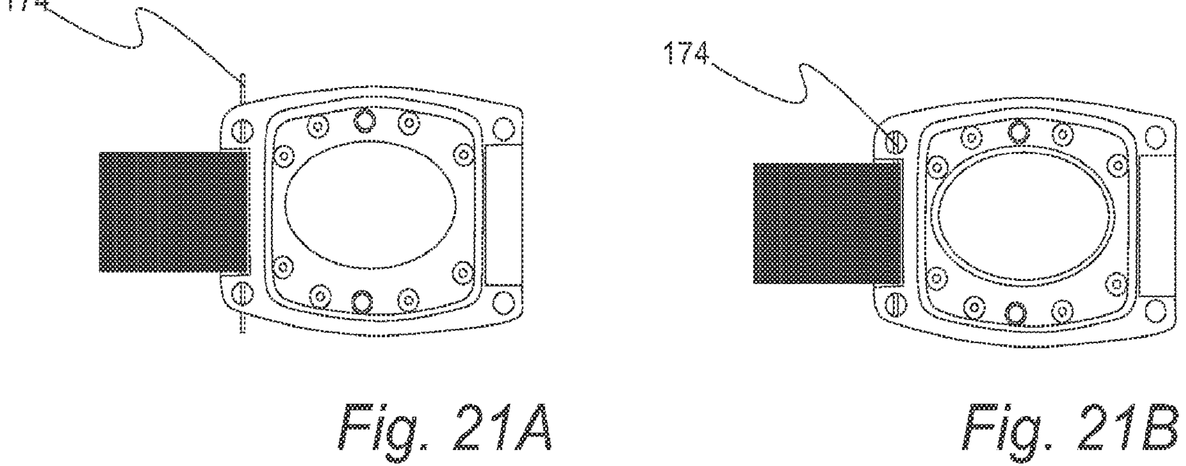
Fig. 21A
Fig. 21B

Which peak qualifies as an alcohol event:

Peak which meets ALL these criteria:

- Peak height above 0.02%
- Peak above 0.02% continuously for 1 hour i.e., t4 - t1 = 1hour
- Peak above 0.03% continuously for 30min i.e., t3 - t2 = 30min
- Rise slope < 0.1%/hour
- Fall slope < 0.035%/hour

NOT AN ALCOHOL EVENT

Rise slope > 0.1%/hour

NOT AN ALCOHOL EVENT

Fall slope > 0.035%/hour

NOT AN ALCOHOL EVENT

Above 0.02% for greater than 1 hour but not continuously
Also above 0.03% for less that 30 min

NOT AN ALCOHOL EVENT

Below 0.02%

Fig. 34

WEARABLE ALCOHOL MONITORING DEVICE

CROSS-REFERENCE TO RELATED APPLICATIONS

This application is the U.S. national phase of PCT Appln. No. PCT/US2023/012167 filed Feb. 2, 2023, which claims the benefit of U.S. provisional application Ser. No. 63/305,811 filed Feb. 2, 2022, the disclosures of which are hereby incorporated in their entirety by reference herein.

STATEMENT REGARDING FEDERALLY SPONSORED RESEARCH OR DEVELOPMENT

The invention was made with Government support under Contract No. R44 AA026119 awarded by the National Institutes of Health. The Government has certain rights to the invention.

BACKGROUND

Alcohol consumption monitoring is used in several legal and health treatment scenarios. Individuals that are incarcerated, on probation, on parole are often monitored for alcohol consumption. Individuals in alcohol treatment programs may also have their alcohol levels monitored. Alcohol consumption can be monitored by breathalyzer tests, blood tests, urine tests, and saliva tests. Although these tests work well, they do not allow the continuous monitoring of alcohol consumption. Transdermal alcohol monitoring provides non-invasive monitoring of alcohol consumption.

SUMMARY

In at least one aspect, a wrist-worn device for monitoring alcohol consumption is provided. The wrist-worn device includes a device housing, an electrochemical sensor, and control circuitry. The device housing includes an upper housing and a lower housing attached to the upper housing. The lower housing includes a top wall and a circumferential side wall. The top wall defines a first access opening. The device housing also includes a wrist piece having a first face and a second face. The wrist piece defines a trench in the first face that protrudes from the second face as a closed curve-shaped protrusion, the closed curve-shaped protrusion configured to fit on a subject's wrist surface such that the closed curve-shaped protrusion presses into a subject's skin to form a liquid and vapor seal inhibiting transdermally emitted ethanol from escaping outside a collection area, the lower housing and the wrist piece cooperatively forming an amplification chamber, the amplification chamber being a cavity below the top wall of the lower housing and above the wrist piece. The wrist piece also defines a plurality of vent holes that allow transdermally emitted ethanol to enter the amplification chamber. The electrochemical sensor for ethanol includes an electrode aligning to the first access opening. The control circuitry is enclosed in the upper housing. The control circuitry is configured to receive measurements from the electrochemical sensor and to calculate transdermal alcohol concentration. The water-absorbing (e.g., a humidity mitigation material or humidity capping material) material is sequestered in the amplification chamber. Advantageously, the wrist-worn device is configured to be continuously worn for at least 30 days if not submersed in water.

In another aspect, the wrist-worn device includes one or more tamper sensors are selected from the group consisting of IR sensors, ambient sensors, humidity sensors, temperature sensors, a strap tamper sensor, and combinations thereof.

BRIEF DESCRIPTION OF THE DRAWINGS

FIG. 19 is a schematic showing a side view of the silicone wristband according to one or more embodiments;

FIG. 20 is a top view showing a top view of the silicone wristband according to one or more embodiments;

FIGS. 21A and 21B is a schematic showing stainless steel pins inserted through an upper housing wristband attachment area and into a silicone wristband hole on each side of the wristband according to one or more embodiments;

FIG. 34 illustrates a history window of the app which shows the data files received by the hardware unit stored by the app in the phone memory according to one or more embodiments;

DETAILED DESCRIPTION

Figure 1A:
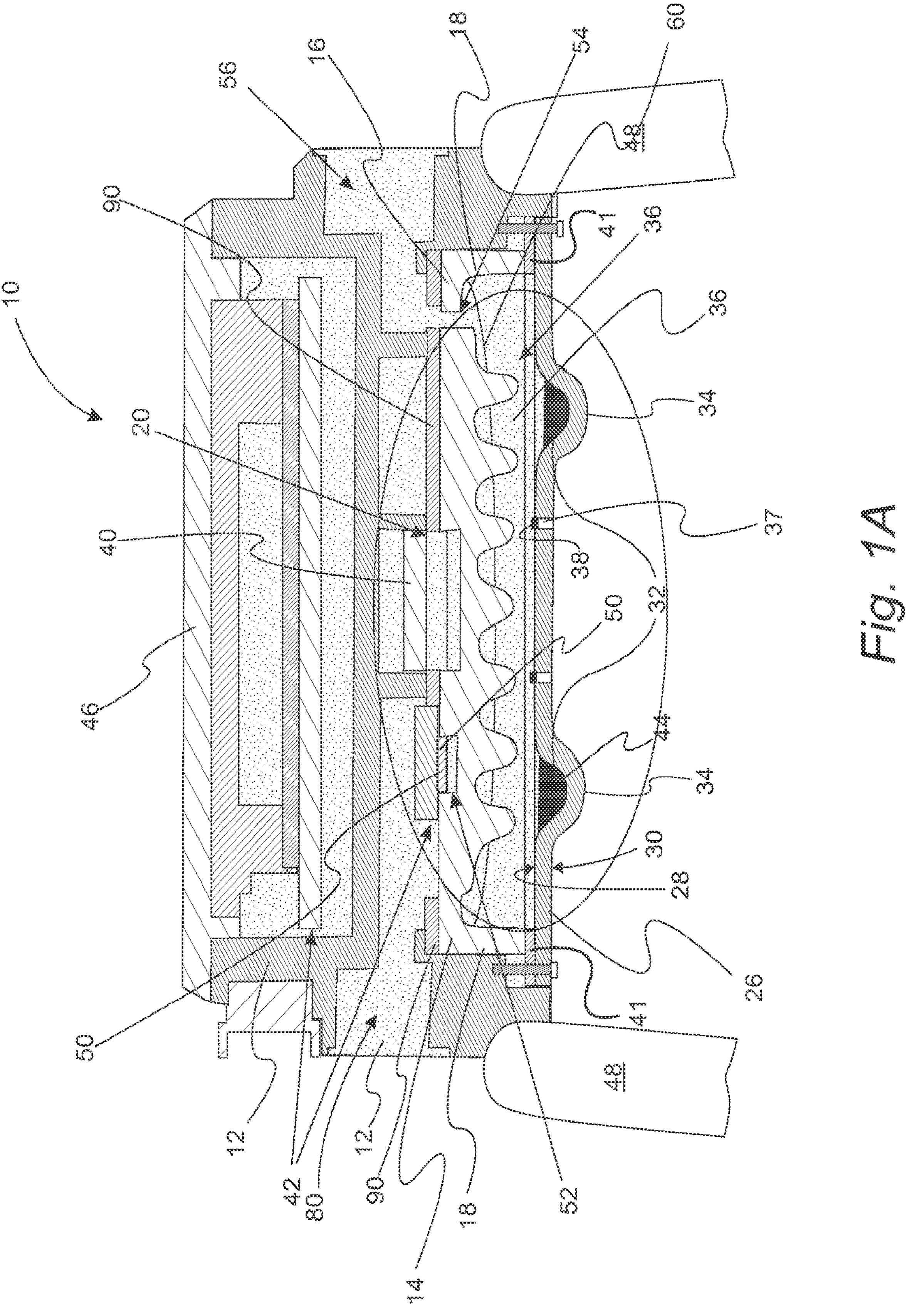
FIG. 1 is a cross-sectional view of an alcohol monitoring device according to one or more embodiments, wherein the collection area is circled.

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The phrase "composed of" means "including" or "consisting of." Typically, this phrase is used to denote that an object is formed from a material.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3. 1.4, 1.5, 1.6, 1.7, 1.8, 1.9, and 2.0 can be selected as lower or upper limits.

When referring to a numerical quantity, in a refinement, the term "less than" includes a lower non-included limit that is 5 percent of the number indicated after "less than." A lower non-includes limit means that the numerical quantity being described is greater than the value indicated as a lower non-included limited. For example, "less than 20" includes a lower non-included limit of 1 in a refinement. Therefore, this refinement of "less than 20" includes a range between 1 and 20. In another refinement, the term "less than" includes a lower non-included limit that is, in increasing order of preference, 20 percent, 10 percent, 5 percent, 1 percent, or 0 percent of the number indicated after "less than."

With respect to electrical devices, the term "connected to" means that the electrical components referred to as connected to are in electrical communication. In a refinement, "connected to" means that the electrical components referred to as connected to are directly wired to each other. In another refinement, "connected to" means that the electrical components communicate wirelessly or by a combination of wired and wirelessly connected components. In another refinement, "connected to" means that one or more additional electrical components are interposed between the electrical components referred to as connected to with an electrical signal from an originating component being processed (e.g., filtered, amplified, modulated, rectified, attenuated, summed, subtracted, etc.) before being received to the component connected thereto.

The term "electrical communication" means that an electrical signal is either directly or indirectly sent from an originating electronic device to a receiving electrical device. Indirect electrical communication can involve processing of the electrical signal, including but not limited to, filtering of the signal, amplification of the signal, rectification of the signal, modulation of the signal, attenuation of the signal, adding of the signal with another signal, subtracting the signal from another signal, subtracting another signal from the signal, and the like. Electrical communication can be accomplished with wired components, wirelessly connected components, or a combination thereof.

The term "one or more" means "at least one" and the term "at least one" means "one or more." The terms "one or more" and "at least one" include "plurality" as a subset.

The term "substantially." "generally." or "about" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

The term "electrical signal" refers to the electrical output from an electronic device or the electrical input to an electronic device. The electrical signal is characterized by voltage and/or current. The electrical signal can be stationary with respect to time (e.g., a DC signal) or it can vary with respect to time.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

As with reference to the Figures, the same reference numerals may be used herein to refer to the same parameters and components or their similar modifications and alternatives. For purposes of description herein, the directional terms "upper," "top", "lower," "bottom," "right," "left," "rear," "front," "vertical," "horizontal," and derivatives thereof shall relate to the present disclosure as oriented in FIG. 1. However, it is to be understood that the present disclosure may assume various alternative orientations, except where expressly specified to the contrary. It is also to be understood that the specific devices and processes illustrated in the drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. The drawings referenced herein are schematic and associated views thereof are not necessarily drawn to scale.

Abbreviations

"SAP" means super absorbent polymer.

"TAC" means transdermal alcohol concentration.

In at least one aspect, a wearable alcohol monitoring device is provided. The disclosed device collects and measures transdermally-emitted ethanol as a measure of alcohol consumption by the wearer. As such, the device can be worn on the wrist, arm region, or other body locations (e.g., ankle). The monitoring may occur for a period of time, such as 90 days, and the device may be substituted at selected time intervals, such as approximately every 28-30 days. The device is tamper-resistant. While the device is disclosed herein with respect to monitoring alcohol, in other embodiments the device could be modified to monitor other biochemical substances such as, but not limited to, ketones.

With reference to FIG. 1, a cross-section of the device is illustrated with the collection area circled. The components of the device are shown in FIGS. 2-12 and described below. The wrist piece is arranged to contact the wearer's skin and may be arranged to be positioned on the top of the wrist. A wrist-worn device 10 for monitoring alcohol consumption is provided. The wrist-worn device 10 includes an upper housing 12 and a lower housing 14. The lower housing 14 includes a top wall 16 and a peripheral side wall 18. Advantageously, the top wall 16 defines a first access opening 20. Lower housing 14 contacts the upper housing 12 and is held in place by the fit and wrist piece 26.

Still referring to FIG. 1, the wrist-worn device 10 further includes a wrist piece 26 having a first face 28 and a second face 30. The lower housing 14 and the wrist piece 26 cooperatively define an amplification chamber 36. Characteristically, the amplification chamber 36 is a cavity below the top wall 16 of the lower housing and above the wrist piece 26 with the sides defined by side wall 18.

Wrist piece 26 defines a trench 32 in the first face 28 that protrudes from the second face 30 as a closed curve-shaped protrusion 34. The closed curve-shaped protrusion 34 is a "donut-shaped" object that is configured to fit on a subject's wrist surface such that the closed curve-shaped protrusion 34 presses into a subject's skin to form a liquid and vapor seal inhibiting transdermally emitted ethanol from escaping outside a collection area defined by the contact of that the closed curve-shaped protrusion 34 with a subject's skin. The seal also prevents contamination from the outside environment (i.e., if the wearer is present in a bar, but not drinking). The wrist piece defines one or more center vent holes 37 that allow transdermally emitted ethanol to enter the amplification chamber 36. Gas-permeable membranes 38 are disposed over or in each vent hole. In a refinement, closed curve-shaped protrusion 34 is substantially circular. While ensuring a good seal on the wrist surface, the diameter of closed curve-shaped protrusion 34 may be maximized to ensure the largest skin area is exposed to the collection path.

Still referring to FIG. 1, wrist-worn device 10 further includes an electrochemical sensor 40 for detecting ethanol. The electrochemical sensor 40 includes an electrode aligning to the first access opening 20. Wrist-worn device 10 further includes control circuitry 42 enclosed in the upper housing. The control circuitry is configured to receive measurements from the electrochemical sensor and to calculate transdermal alcohol concentration. Typically, the control circuitry includes a microprocessor.

In a variation, a water-absorbing material 44 is sequestered in the amplification chamber 36 for absorbing water vapor and/or liquid water as described below in more detail. In a refinement, water-absorbing material 44 is held in trench 32.

Still referring to FIG. 1, top cover 46 is attached to the device over upper housing 12. Finally, a tamper-resistant wristband 48 is attached to wrist-worn device 10 in order to secure the device to a human subject having their ethanol consumption monitored.

Figure 2A:
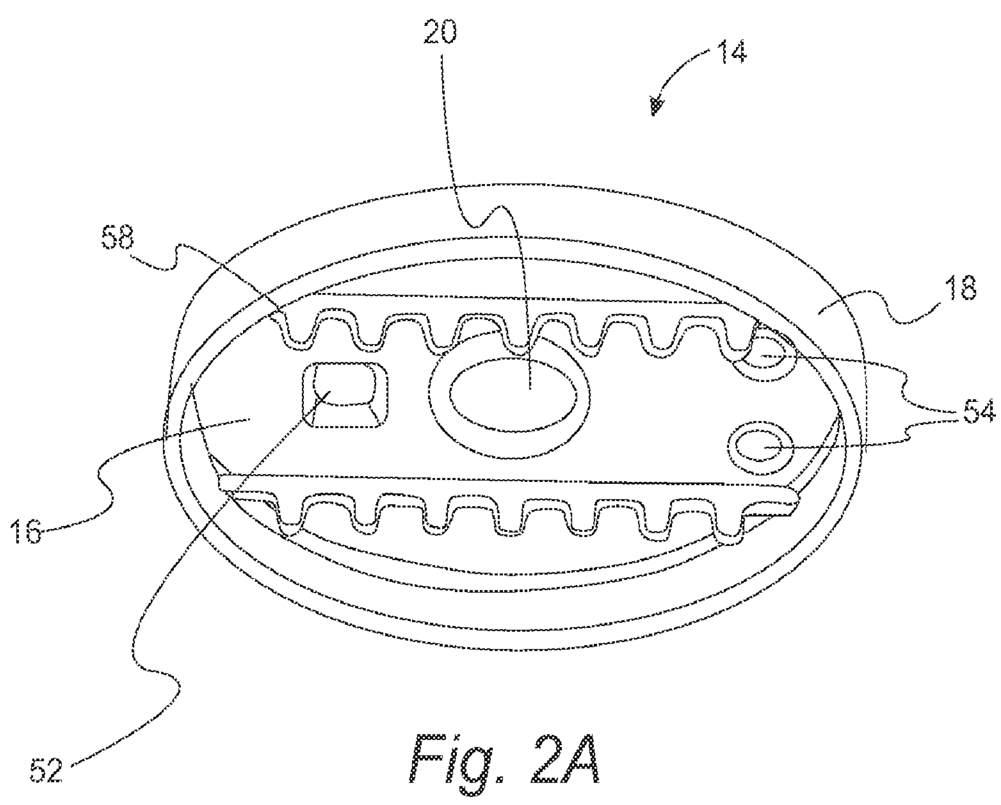
FIG. 2A shows a bottom perspective views of a lower housing of the device according to one or more embodiments.
Figure 2B:
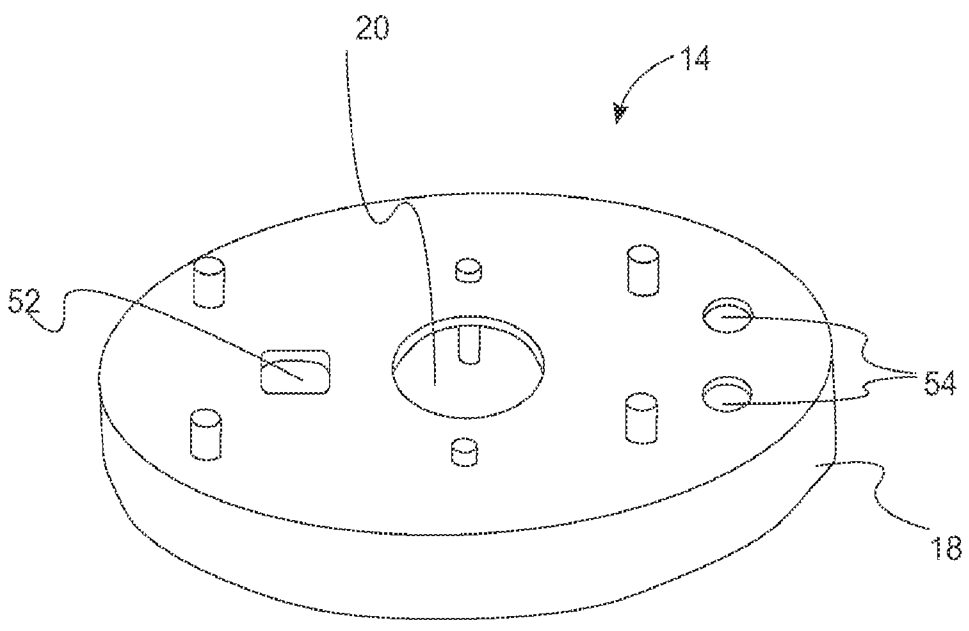
FIG. 2B shows a top perspective views of a lower housing of the device according to one or more embodiments.

With reference to FIGS. 1 and 2, the bottom of the lower housing 14 partially forms the amplification chamber 36 which collects ethanol that is emitted from the skin and passes through vent holes 37 and gas-permeable membranes 38 in the metal wrist piece 26. The volume of this amplification chamber 36 is directly proportional to the monitored ethanol signal. First access opening 20 at the top of the amplification chamber allows ethanol to pass through to the electrochemical sensor 40 mounted on the top of the lower housing 14. In a refinement, electrochemical sensor 40 is a custom electrochemical sensor that monitors ethanol vapor. It should be appreciated that other biochemical sensors are also contemplated for use with the device disclosed herein. In a refinement, the anode of electrochemical sensor 40 is exposed to the amplification chamber 20. The change in electrical current through electrochemical sensor 40 is proportional to the amount of ethanol that contacts the platinum-coated anode. The conductivity of electrochemical sensor 40 is affected by relative humidity (RH) and temperature. Therefore, RH is measured by a humidity/temperature sensor 50. In a refinement, a humidity/temperature sensor 50 is mounted on a printed circuit board (PCB) and exposed to the amplification chamber 36 through a second access opening 52 (e.g., a square hole) on the left side of the lower housing in FIG. 2. The circuit board mounted on the top of the lower housing will be further described below.

Still referring to FIGS. 1 and 2, the amplification chamber defines opening(s) 54 in fluid communication with vent path conduit 56 for vapors emanating from the skin to be removed from the amplification chamber. In a refinement, the two rows of "fences" or "teeth" 58 on the bottom of the amplification chamber may be used to secure pouches 60 which hold water-absorbing material 44. In a refinement, lower housing 14 is composed of a polymer that is compatible with water and ethanol over the range of operating temperatures. Moreover, such polymers will be low-cost and machinable. Examples of such polymers include, but are not limited to, polypropylene, ABS plastic, and the like.

Figures 3, 4A, 4B:
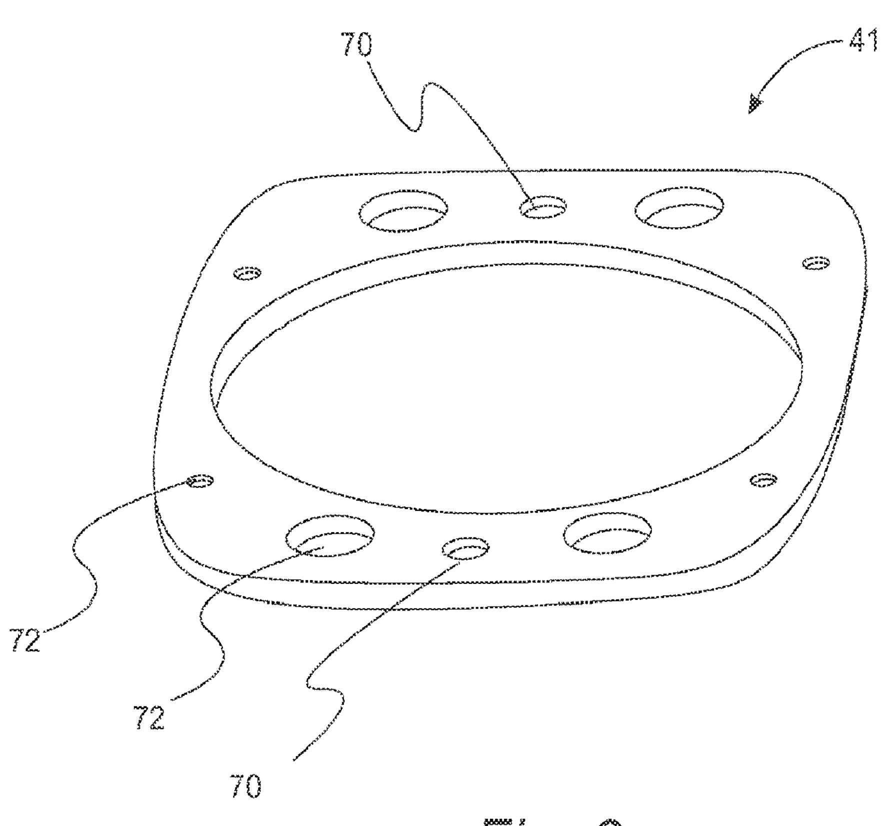
FIG. 3 is a perspective view of a lower gasket of the device according to one or more embodiments.
FIG. 4A shows a bottom perspective views of a wrist piece of the device according to one or more embodiments.
FIG. 4B shows top perspective views of a wrist piece of the device according to one or more embodiments.

Referring to FIGS. 1, 3, and 4, lower gasket 41 is interposed between the peripheral side wall 18 and wrist piece 26. In a refinement, the bottom gasket may be cut from a polymeric sheet or other suitable sealing material. For example, the bottom gasket 41 can from a 1/16" VITON® sheet. The bottom gasket 41 can also be compression molded or injection molded. VITON is compatible with water and ethanol vapor over the full range of expected operating temperatures. The bottom gasket allows the metal wrist piece to seal to the top housing 12 (e.g., made from polypropylene or any other suitable polymer) and to the bottom housing 14 thereby preventing water liquid or water vapor or any liquid/vapor from seeping into the device. A portion of bottom gasket 41 can also extend into the bottom of the amplification chamber 36. Ethanol vapor emitted from the skin will pass through the gas-permeable membranes 38 and enter the amplification chamber 36 before reaching the sensor. The bottom gasket 41 ensures that the lower housing 14 (e.g., made from polypropylene, ABS plastic, and the like) forms a consistent, repeatable seal to the metal wrist piece 26 while forming the amplification chamber. This will minimize unit-to-unit variation for the amplification chamber across multiple units. The bottom gasket has through-holes 70 for the polycarbonate rods, described further below with respect to tamper resistance, and holes 72 (e.g. 8 holes) for the sealing screws that attach the metal wrist piece to the top housing.

Referring to FIG. 4, the diameter of closed curve-shaped protrusion 32 is maximized to ensure the largest skin area is exposed to a collection path. The more skin exposed to the collection path, the more potential sites for transdermally-emitted alcohol. Typically, closed curve-shaped protrusion 32 has an inner diameter that is small enough to completely fit on the top surface of the wrist size ranges in the US adult population. The height of the closed curve-shaped protrusion 32 is configured to ensure that ethanol molecules emitted from the skin can sufficiently diffuse through the one or more vent holes 37 (e.g., four) on the metal surface inside the closed curve-shaped protrusion 32. In one or more embodiments, each of these vent holes is covered by a gas-permeable membrane 38. The gas permeable membranes 38 are not selective to gases. In a refinement, gas-permeable membranes 38 are made from ePTFE, which non-selectively allows gas molecules (e.g. water vapor, oxygen, ethanol vapor) to pass while providing a barrier to liquid and dust. This surface with the four holes may be constructed with a solid material to avoid exposing the sensor within the device to abrupt spikes in humidity and temperature. The bottom-most surface of the closed curve-shaped protrusion 32 may be curved to ensure the best comfort on the wearer's skin. The bottom-most surface of the closed curve-shaped protrusion 32 may also be curved at the edges (like a saddle) to better conform to the wearer's wrist.

With reference to FIG. 4, wrist piece 26 can be composed of a metal, and in particular, a hypoallergenic metal. For example, wrist piece 26 can be composed of titanium (e.g., Grade 1) to be hypoallergenic-compatible, and may be machined through CNC machining and/or stamping. Other options for the wrist piece material include nickel-free stainless steels, such as BIODUR®. Typically, wrist piece 26 includes holes around its perimeter. These holes allow for two types of components. In the center of the left and right sides, there are hole(s) 76 for an IR transparent rod (e.g., polycarbonate rod) to pass through. This will be discussed further below with respect to the tamper resistance of the device. There are also holes 78 (e.g., eight) in the wrist piece for sealing screws to attach to the upper housing 12. For this purpose, special screws may be used that are stainless steel. The screws may have specially designed gasketing (e.g., VITON®) attached to the screw to ensure sufficient waterproofing when the screws are used to fasten the wrist piece to the top housing. In a refinement, a Locite threadlocker adhesive is used to secure the screws against water ingress.

The heads of the screws (the side exposed to the wearer's skin) may be coated with up to 2000 A of titanium.

In addition to ethanol vapor, the skin emits other vapors as well including water vapor (i.e. sweat). The custom sensor performance is affected by relative humidity and can be damaged if contacted with liquid water. Even if liquid water does not enter the device, liquid water can still be generated through condensation. For example, if a great deal of water vapor enters the device and is trapped inside, a significant drop in temperature could result in liquid water formation through condensation. As set forth above, a water-absorbing material 44 is sequestered in the amplification chamber for absorbing water vapor as described below in more detail. Particularly water vapor absorbing material is super absorbent polymer (SAP). Water-absorbing material 44 is typically a humidity mitigation material or humidity capping material. If the device is well sealed as it should be, water should not enter the unit. SAP helps with humidity not reaching to high values e.g., above 90% that is close to condensation condition. An example of such materials includes, but are not limited to, sodium polyacrylate, which may be utilized in the device disclosed herein to address humidity. The SAP material (e.g., sodium polyacrylate) may be used because it has been verified to be the most absorbent (by weight and volume) for water vapor compared to other desiccant-type materials (e.g., molecular sieves, silica gel). Also, SAPs do not absorb alcohol, such as ethanol vapor. Therefore, the selectivity of water absorption to ethanol vapor absorption is very high. Lastly, the absorption is stable—as temperature increases, other desiccants release the water vapor that has been absorbed. However, SAPs hold onto the water as temperature increases. In one or more embodiments, sodium polyacrylate may be used in a fine granular form or a powder form. It may be secured in trench 32 in the metal wrist piece by a fine stainless-steel mesh that is epoxied over the valley after the SAP has been added. Alternatively, the SAP (e.g., sodium polyacrylate) could be disposed within a pouch. Advantageously, the inclusion of the SAP material is an inexpensive and reliable way to maximize ethanol flow without moving parts while addressing humidity issues with the fuel cell architecture of the sensor.

Referring again to FIG. 2, the bottom of the lower housing 14 incorporates one or more vent holes 54 (e.g., two) on the right side. These holes allow water vapor, and some ethanol vapor, to escape from the amplification chamber. The gas flow rate through the vent holes is controlled by a) the size of the holes; and b) the gas flow rate of the gas permeable membrane chosen to cover the vent holes in the lower housing.

Figure 8:
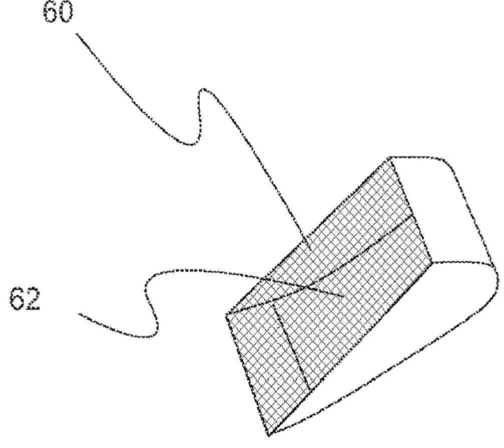
FIG. 8 is a perspective view of an additive pouch of the device according to one or more embodiments.

Referring to FIGS. 1, 2, and 8, "fences" or "teeth" 58 on the bottom of the amplification chamber may be used to secure pouches 60 which hold water-absorbing material 44. In a refinement, two rows or sets of fences or teeth, on the bottom of the lower housing 14 may be used to secure additive pouches 60. Additive pouches 60 are thermoformed hollow wedges which may be made from, for example, DuPont TEFZEL®. As mentioned above, these pouches may also hold an SAP material such as sodium polyacrylate for water vapor absorption. After the SAP is added to the pouches, a fine stainless-steel mesh may be epoxied to the open side of the wedge, and the piece then inserted in the lower housing. In a refinement, two additive pouches are inserted in total. In another embodiment, the retaining wall (fence or teeth) may be modified so that only the outermost teeth or fenceposts on either side will remain, so as to ensure as much unrestricted air flow as possible into the pouch with the sodium polyacrylate. In a refinement, the fine stainless-steel mesh 62 may be epoxied to the open side of the wedge to contain the SAP using a fast-curing epoxy (e.g., 10 seconds) with no or low VOCs (volatile organic compounds), such as DUV curable epoxy. The fast-curing epoxy could alternatively be used to affix the stainless-steel mesh to contain the SAP at other locations (e.g., covering the valley).

With reference to Figures and 6A and 6B, perspective views of top housing 12 are provided. Top housing 12 has vent path conduit 56 for the venting of the amplification chamber in the lower housing as described above. On the other side, vent conduit 80 is formed for the venting of the chamber above the lower housing 14 where the custom sensor is installed. In a refinement, the second vent conduit is configured for providing air flow or oxygen flow to the electrochemical sensor in a space above the upper housing. Also depicted are bosses 82 that hold anchors for the screw attaching wrist plate 26. Boss 84 has a center bore that IR transparent rod 86 (e.g., a polycarbonate rod) for the tamper detection system.

Figure 7:
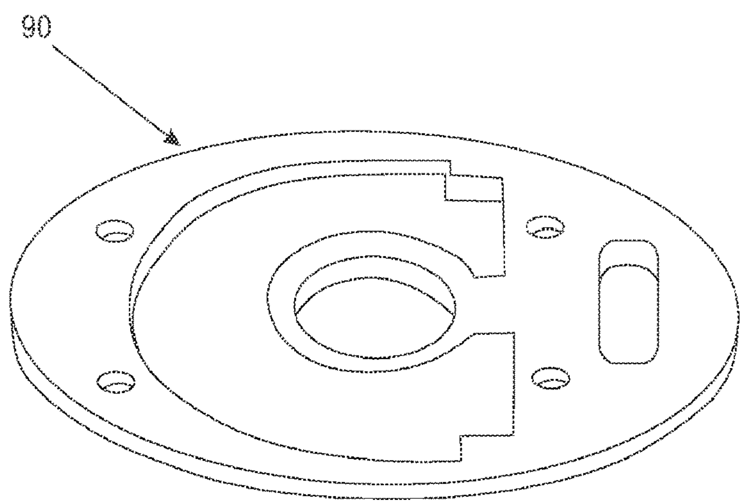
FIG. 7 is a perspective view of an upper gasket of the device according to one or more embodiments.

With reference to FIGS. 1 and 7, upper gasket 90 is used to seal lower housing 12 to upper housing 14. Upper gasket 90 can be composed of a polymeric material. For example, upper gasket 90 may be cut from 1/16" VITON® sheet. The upper gasket 90 may also be compression molded or injection molded. VITON® is compatible with both ethanol and water vapors for the operating temperature range. The right side of upper gasket 90 as depicted in FIGS. 1 and 7 seals the vent path from the lower housing to the upper housing.

Figure 5:
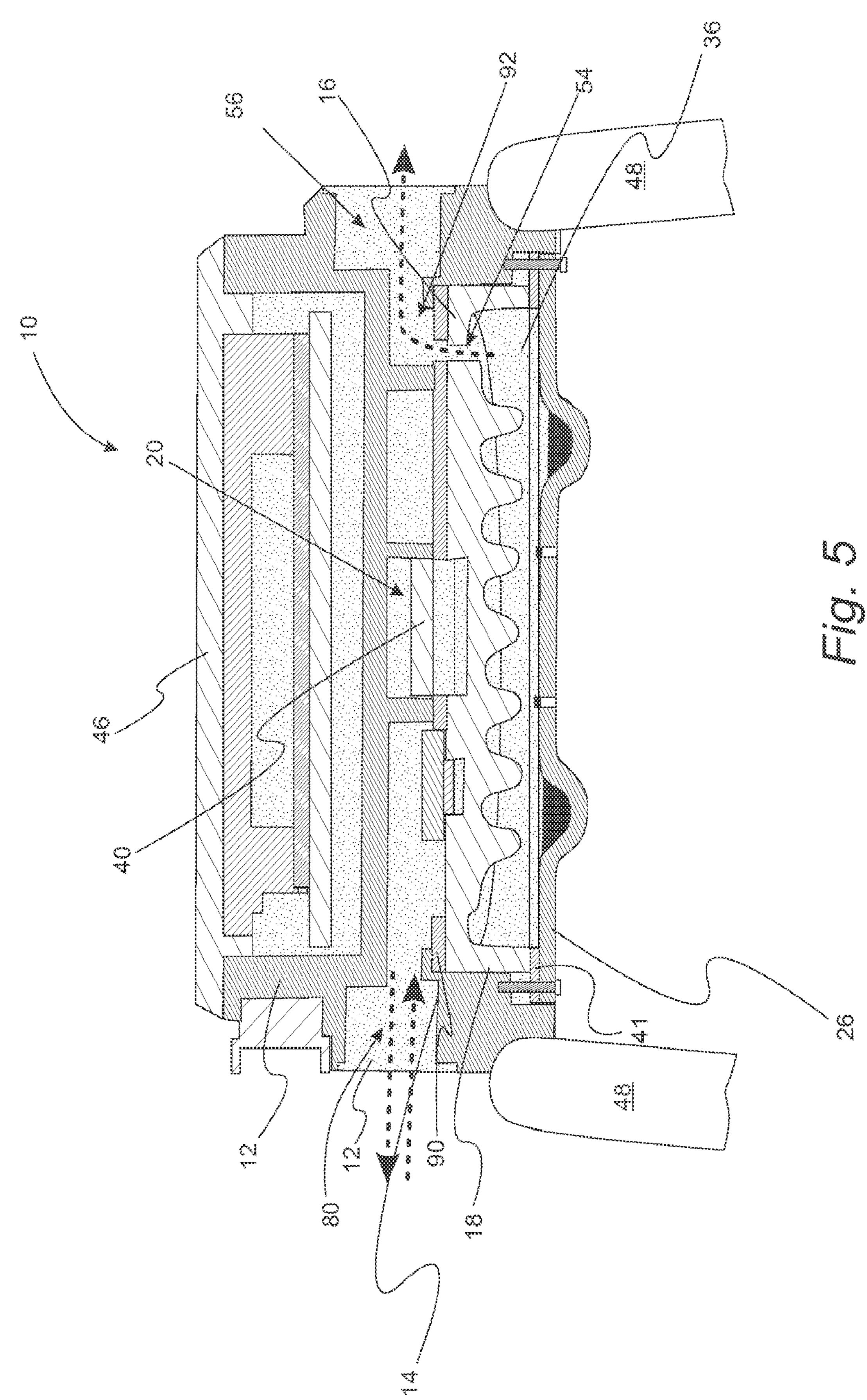
FIG. 5 is a cross-sectional view of the alcohol monitoring device showing vent paths indicated with arrows.

The vent path through the top housing is illustrated in FIG. 5. On the right, towards the bottom of the image, the "plumbing" 92 for vent conduit 56 is illustrated that allows vapor to flow from the amplification chamber 36 in the lower housing. Once inside the plumbing, it is redirected 90 degrees to allow vapor to flow out of the device.

Figure 9A:
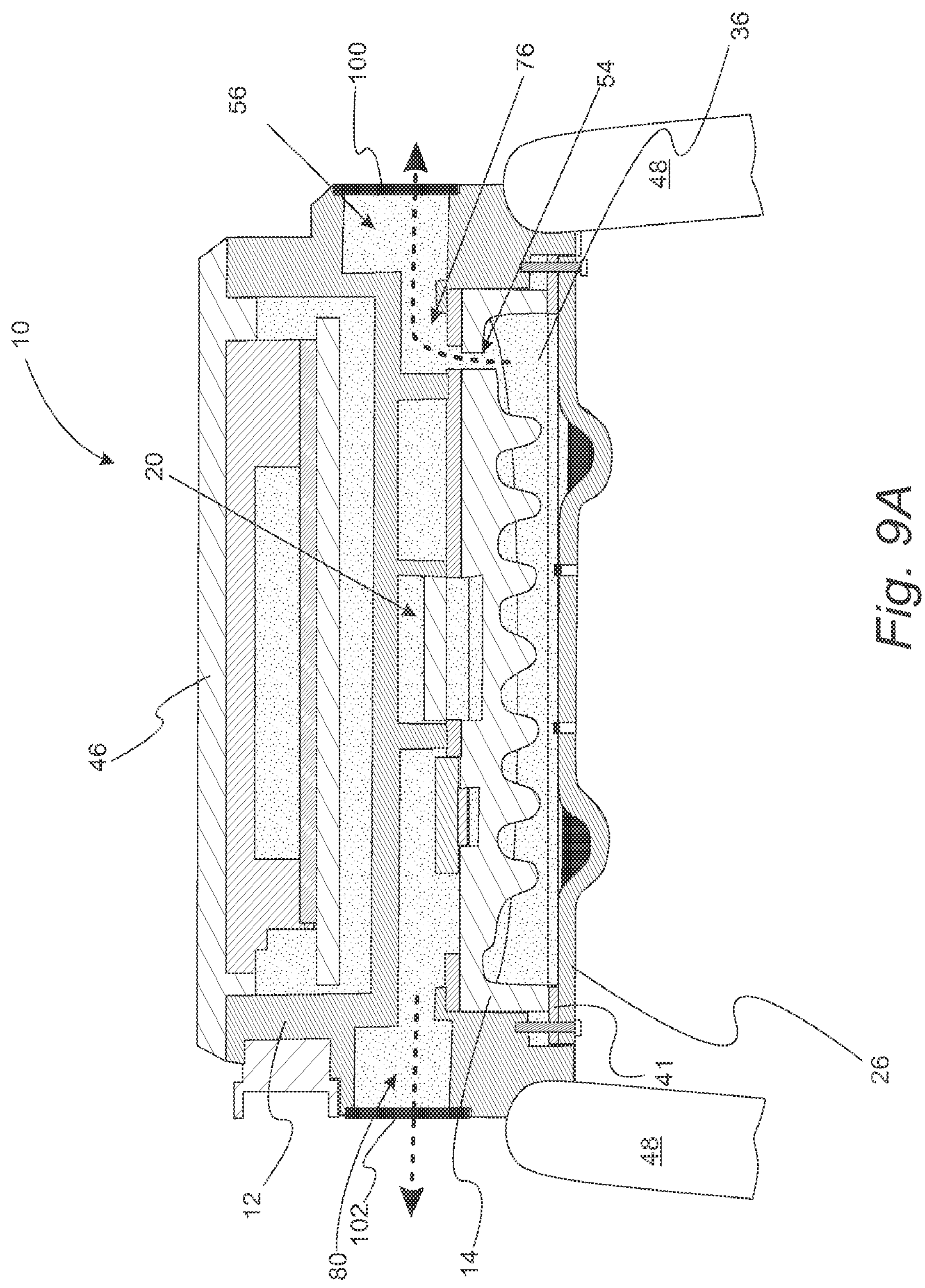
FIG. 9A illustrates steam guards for installation within a vent path of the device according to one or more embodiments.
Figures 9B, 9C:
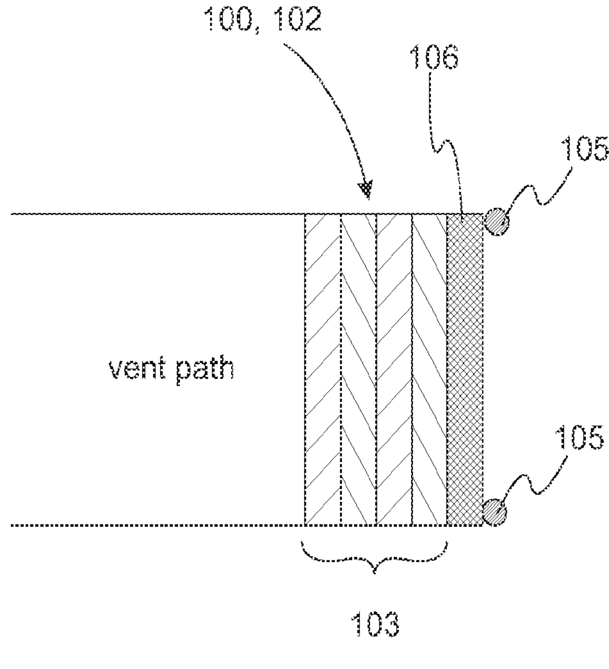
FIG. 9B provides a cross-section of a variation of a steam guard.
FIG. 9C provides a cross-section of a variation of a steam guard.

With reference to FIGS. 9A, 9B and 9C. "steam guards" 100 and 102 are provided for installation within these vent paths. The steam guards stop liquid water flowing into devices 10. As mentioned above, the gas-permeable membranes are not selective for which gases pass through—the ePTFE of the membrane is inert for the operating temperatures of the device. In a variation, the steam guards may include multiple layers of pyrolytic graphite 103 which is highly thermally conductive. In another variation, the steam guards may include multiple layers of compressed metal foams 104, e.g., nickel foam thermally conductive which are thermally conductive. The multiple layers create a torturous path to ensure that gas molecules will contact the layers as they propagate through the multiple layers. Water vapor (e.g., hot steam) will contact the materials, lose heat/energy, and condense before propagating completely through the steam guards. Other gases (e.g., nitrogen, oxygen, ethanol vapor) will not react chemically with pyrolytic graphite or metal foams in the steam guards and thus can propagate through the multiple layers. In one or more embodiments, the pyrolytic graphite may be held within stainless steel rings 105. The outermost layers of the pyrolytic graphite may be protected from structural damage (e.g., punctures or tearing) by a fine stainless-steel mesh 106. The outside of the steam guards may be protected from dust/liquids by a gas-permeable membrane and another layer of stainless-steel mesh. The mesh edges may be covered by a thin plastic square. In one or more embodiments, from most inner to most outer, the components are: steam guard, gas permeable membrane, stainless steel mesh, and plastic square with a hole inside.

As described above, top housing 12 also has a vent path 80 to the outside of the device that allows air to flow from the area containing the custom sensor. In addition, air can flow in through vent path 80. In one or more variations, the custom sensor requires oxygen to maximize performance. The vent path with the steam guard, similar to what is defined for the vent path 56 from the amplification chamber, limits water flow inward, as water in liquid form could damage the custom sensor.

Figure 6A:
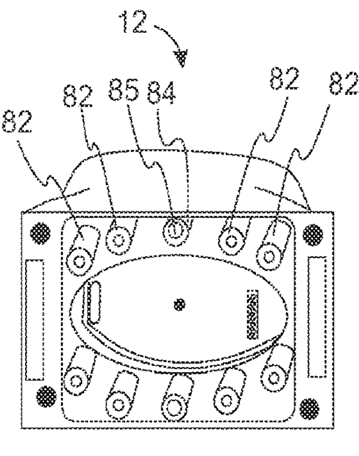
FIGS. 6A and 6B, shows bottom and top perspective views of a top housing of the device according to one or more embodiments.
Figure 6B:
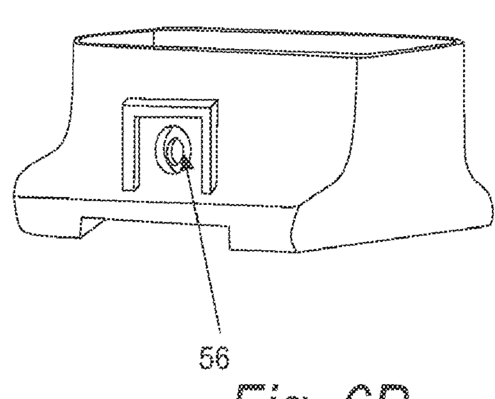
Figure 10:
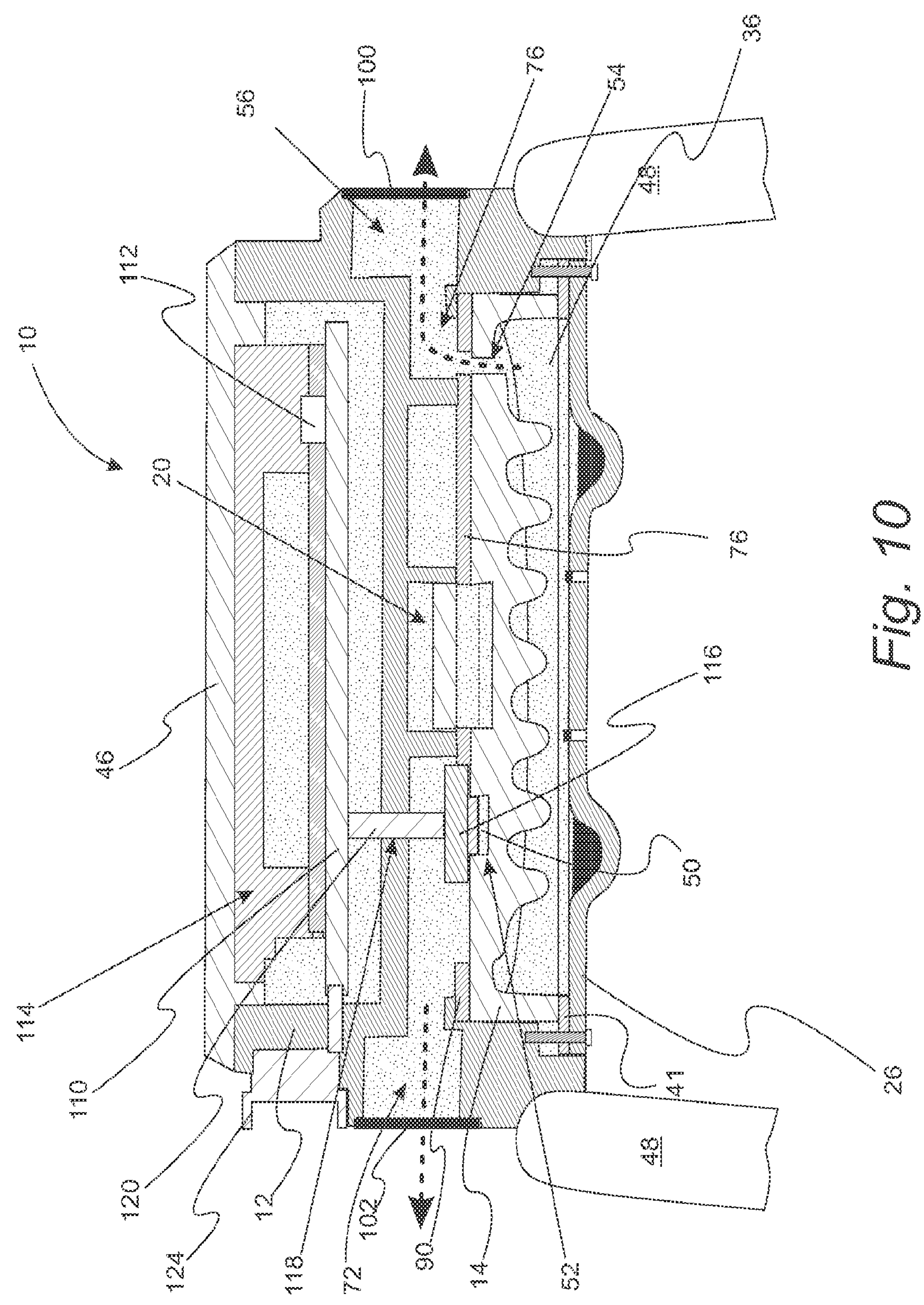
FIG. 10 is a cross-sectional view of the alcohol monitoring device illustrating circuit board installation according to one or more embodiments.

With reference to FIG. 10, a cross-sectional view of the device is illustrated which shows the installation position of the circuit board. The primary PCB 110 and battery 112 are installed in compartment 114 located in the top housing 12 (FIG. 6). Primary PCB 110 is in electrical communication with daughter board 116. A slot 118 in the compartment allows pogo pins 120 from the primary PCB 110 to electrically contact the daughter board 116. The humidity, voltage, and temperature readings from the daughter board will eventually be processed and transmitted via Bluetooth from the primary PCB. In a refinement, because of the opening in the bottom of the compartment, the primary PCB and the battery are conformally coated, such as with HUMISEAL 1B51, which provides protection against corrosion and chemical attack.

Figure 11A:
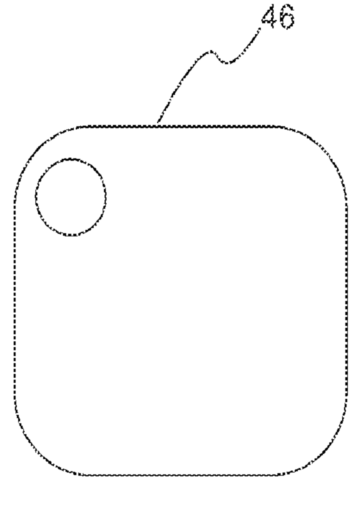
FIGS. 11A and 11B are top and bottom perspective views of a top cover of the device according to one or more embodiments.
Figure 11B:
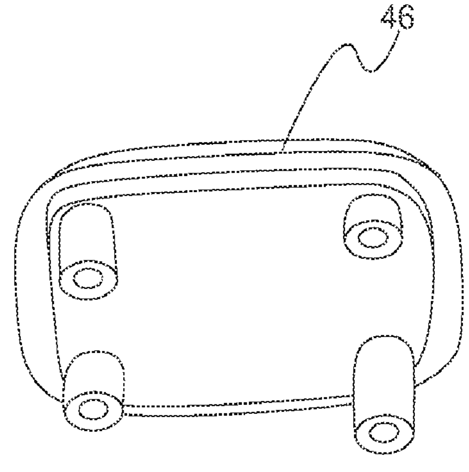

With reference to FIGS. 11A and 11B, the top cover 46 is attached to the top housing. This can be accomplished by using four screws. Two of the screws are routed through the PCB 110. The two shorter bosses 130 on the top cover will press down onto the PCB to secure it. A thin donut (e.g., VITON) may be used to provide a compressible barrier between the top cover (e.g. composed of polypropylene, ABS plastic, and the like) and the circuit board. The top cover may have a translucent window to allow viewing of an indicator LED on the PCB. A gasket (e.g., VITON) may be used to waterproof the top cover against the top housing.

In a variation, the primary PCB 110 has mounted a micro USB connector 124 for data transmission and battery charging. In a refinement, a USB cover is used to cover the USB connection to provide waterproofing. A USB cover may be used to protect the micro-USB port on the primary PCB from liquid water (e.g., while showering) and to prevent access to the board electronics by a wearer. The USB cover may be press fit and sealed (e.g., with PTFE) such that it is secure and cannot be removed with the top cover screwed on. In an alternative embodiment, a custom micro-gasket made from VITON may be used in place of the PTFE sealing. The USB connection is used for battery charging, data transfer and board diagnostics. In a refinement, the daughter board is mounted on the top of the lower housing (FIG. 2) such that the humidity sensor 50 on the daughter board 96 bottom fits through the hole 52 (shown on left side) in the lower housing.

Figure 12:
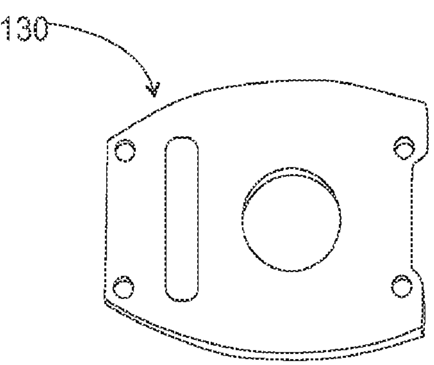
FIG. 12 is a top view of compression plastic for the device according to one or more embodiments.

With reference to FIGS. 10 and 12, the custom sensor 40's anode is centered on a ring in the center of the upper gasket 90. The custom sensor is compressed against this gasket by a thin polycarbonate sheet 130. This polycarbonate sheet also compresses the custom sensor onto the daughterboard. Finger springs are soldered onto gold pads of the daughter board. The copper contacts from the custom sensor are compressed by the polycarbonate sheet against the finger springs. The polycarbonate sheet is aligned onto four bosses located on the top of the lower housing. Small donuts (e.g., VITON) may be pressed down on/over the bosses to secure the polycarbonate sheet in place, forcing the custom sensor to press down against the inner VITON ring (on the upper gasket) and against the finger springs on the daughter board 96. The transparency of the polycarbonate allows one to monitor the alignment of the custom sensor 40 while it is being secured. Pogo pins 120 from the primary PCB 110 extend and contact pads on the daughter board to allow humidity, temperature, and voltage signals from the daughter board to be transmitted.

FIGS. 13 to 17 illustrate various components for wristband attachment to the device. In one or more embodiments, the device is attached to the wearer's wrist or other arm region with a silicone wristband 48. Other body attachment regions such as, but not limited to, the ankle are also contemplated. The wristband may be attached to the device by securing compressible rods 152 which feed through the wristband into "arms" 154 that extend from either side of the upper housing 12. As shown, there may be multiple feedthrough cylinders 156 in the wristband to allow the wristband to be trimmed to a correct fit for a particular wrist size. Additional cylinders may be cut off during installation. The wristband 48 also includes a substantially flat region 158 connecting regions having the feedthrough cylinders.

A metal plate 160 may be used to prevent erosion/damage of top housing arms (e.g., polypropylene) as the metal rod is inserted. An awning over the rod may be used to make the rod less accessible and more tamper-resistant. Silicone inserts 162 (FIG. 15), installed on the bottom, stabilize the device to prevent rotation and prevent liquid water (e.g., during showering) from potentially encroaching into the collection area. The wristband is a consumable and will be cut (destroyed) to be removed (e.g. after 30 days of wear).

Figures 13, 14, 15, 16, 17:
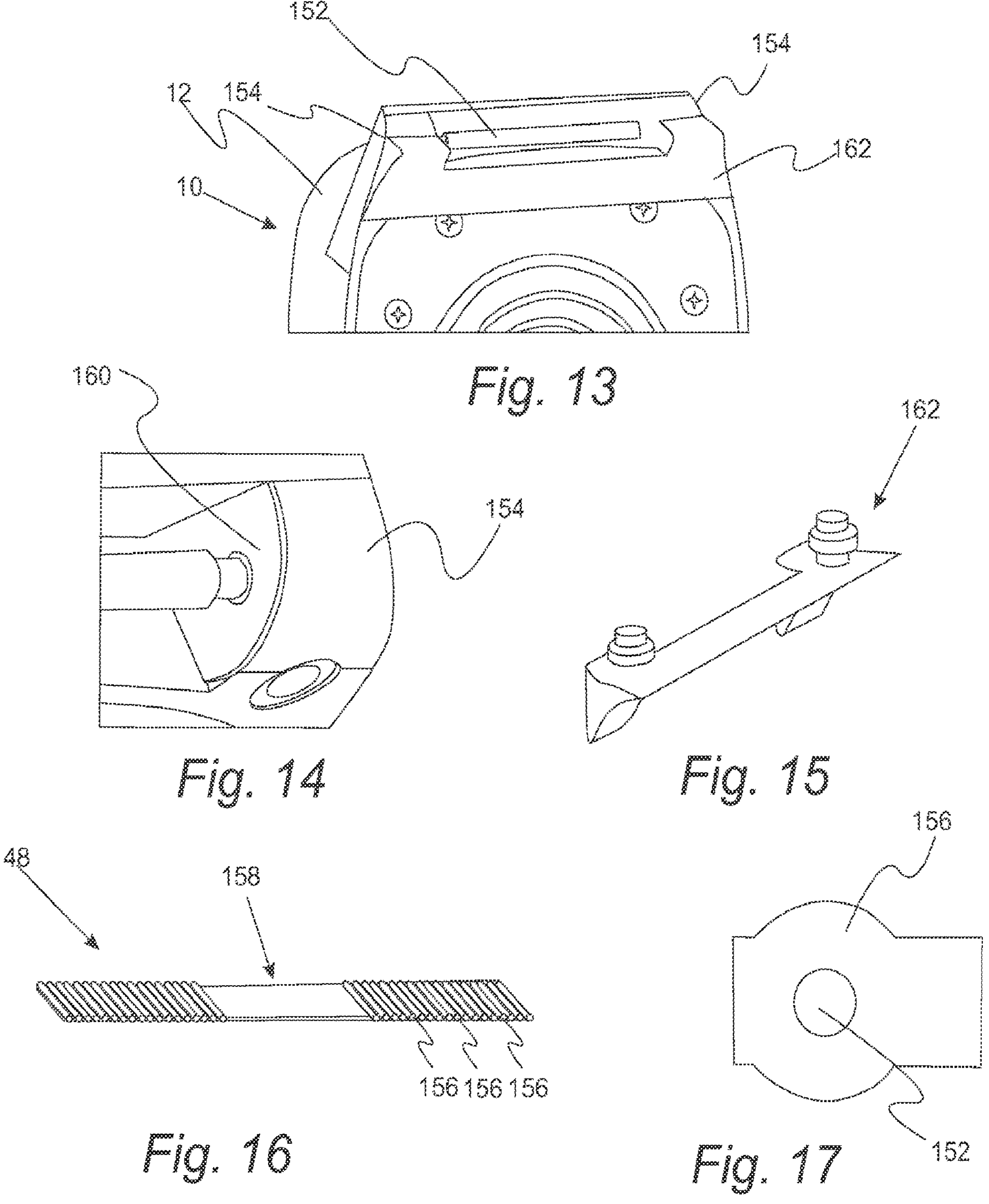
FIG. 13 is a perspective view illustrating an attachment mechanism for a wristband of the device according to one or more embodiments.
FIG. 14 is an enlarged view of a portion of FIG. 18 illustrating a rod to the top housing in the device according to one or more embodiments.
FIG. 15 is a perspective view of silicone inserts for the device according to one or more embodiments.
FIG. 16 is a perspective view of a silicone wristband of the device according to one or more embodiments.
FIG. 17 is a side view of the wristband illustrating a through hole for the rod of the device according to one or more embodiments.
Figure 18:
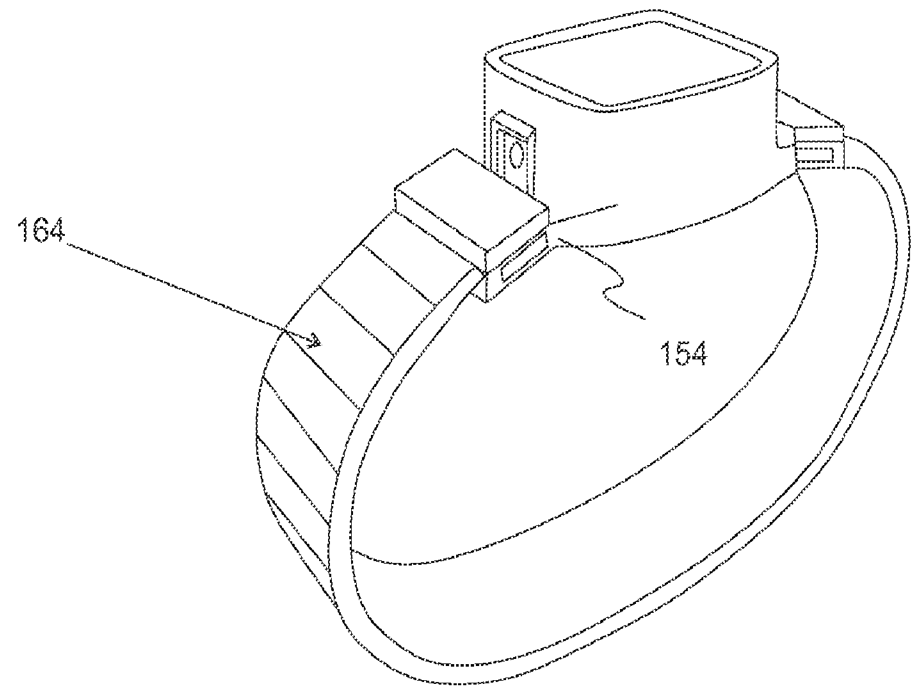
FIG. 18 is a schematic illustration of cutting the wristband strap along one of its creases according to one or more embodiments.

With reference to FIG. 18, the silicone wristband 48 may be modified to be without the smooth flat region 158 of FIG. 16. Instead, the silicone strap 164 may be the same thickness for its entire length, smooth on the bottom, and creased on the top where cuts are to be made to size the strap according to wrist size, with through holes for the entire length of wristband. In this embodiment, the wristband is attached to the device with metal (stainless steel) or plastic rods which feed through the wristband into the "arms" that extend from either side of the top housing. The arms 154 have a through hole to allow the rods to pass through to be riveted at the end using a custom tool to make the fastening mechanism secure from tampering.

With reference to FIGS. 19-21, another wristband and tamper-resistant attachment for the device is depicted. FIG. 19 shows a side view of the silicone wristband. The top may be serrated to guide the field service team in trimming the wristband length to best fit the size of the wearer's wrist. The bottom may be smooth for maximum comfort on the wearer's wrist. In one non-limiting embodiment, the holes may be 1.7 mm in diameter, and the stainless steel pins may be 2.0 mm in diameter so that the wristband compresses ("grabs") onto the pins. FIG. 20 shows a top view of the wristband. The 1.7 mm holes do not extend completely through the wristband. There is a solid segment of silicone in the middle of the strap which prevents the pins in each hole from being pushed through by the wearer (this would allow the pins to be removed which would allow the wristband and device to be removed). In another embodiment, the solid segment of silicone in the middle of the strap may contain metal wires 172 which make an electrical connection through the housing to the primary PCB. In the event that a strap is cut by the wearer, the electrical connection is broken, thus indicating tampering. In another embodiment, the solid segment of silicone in the middle of the strap can contain an optical fiber that couples with an LED at one end and a photodiode at the other end in the housing. In the event a strap is cut by the wearer, the optical path is broken and can be detected, indicating tampering.

With reference to FIGS. 21A and 21B, the stainless steel pins 174 are inserted through the upper housing wristband attachment area and into the silicone wristband holes on each side. The pins are fully inserted into the wristband so that the pins do not extend past the plastic housing, such that they will not be accessible for removal. The silicone inserts 162 may align with the through hole in the arms to allow the stainless steel pins 174 to go through and provide added stability.

With reference to FIGS. 21A and 21B, the pins are fully inserted and depressed in holes in the upper housing, and they will not be accessible for removal. The ends of the pins are flat, and without a head to access the pins.

Figures 22A, 22B:
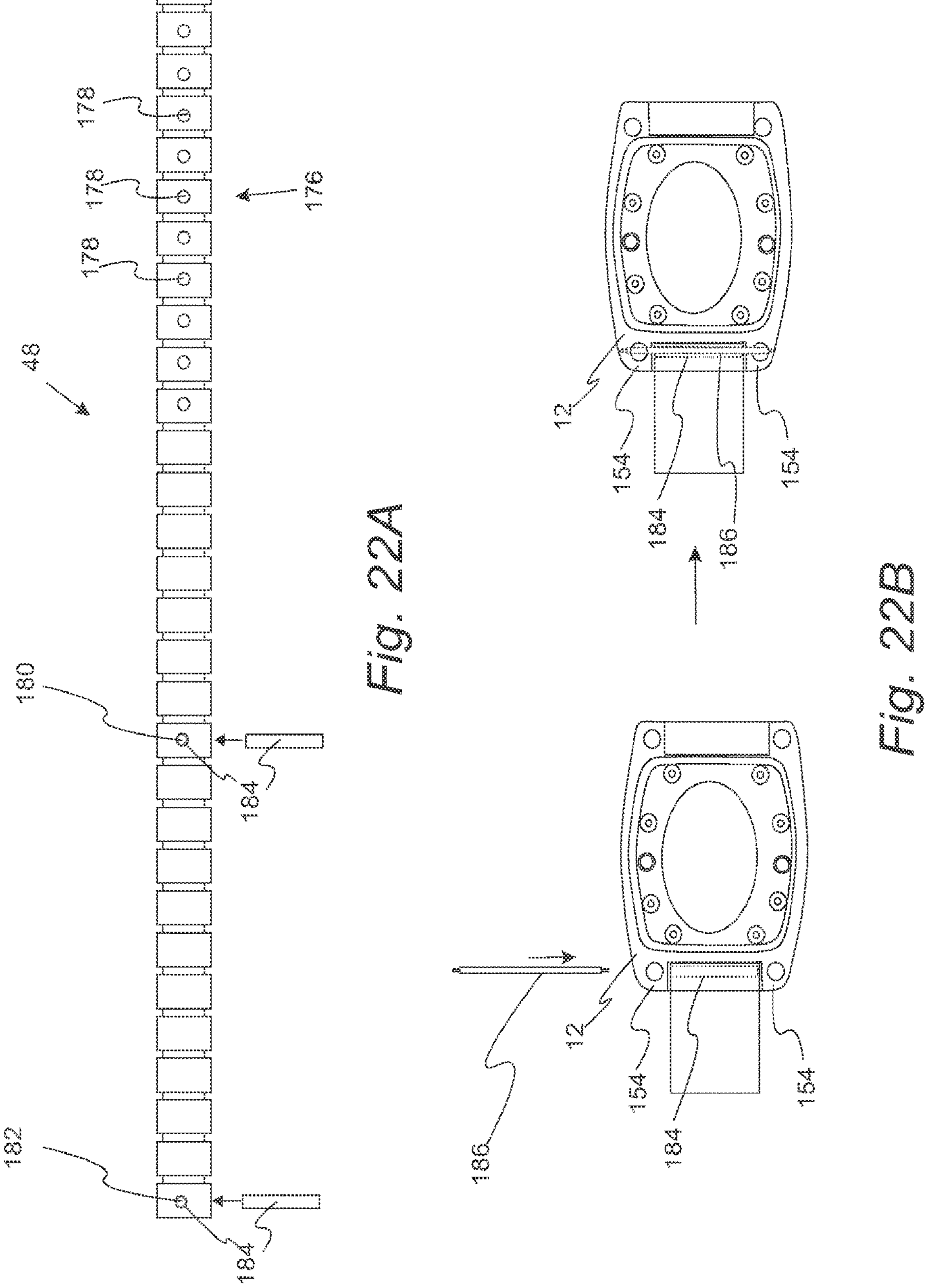
FIGS. 22A and 22B is a schematic showing the pins fully inserted into the wristband according to one or more embodiments.

FIGS. 22A and 22B depict another variation of wristband 48. In this variation, wristband 48 is a serrated band in which the serration defines a plurality of sections attached together. The serrations guide the trimming of the wristband to the length that best fits the wrist of a human subject whose alcohol consumption is being monitored. In a refinement, the serration can be limited to only one side of the wristband. The wristband 48 includes a plurality of through holes 178 for sizing. The wristband also includes anchor point hole 180 for small wrist sizes and anchor point hole 182 for larger wrist sizes. In a refinement, there are partial holes through the wristband sections that allow flexibility and comfort. A hollow tube 184 into the band first. Then when the assembly on the wrist is happening the final step involves an end-to-end dowel pin. For wristband installation, one unit arm 154 of upper housing 12 is blocked while the other arm 154' has an opening for placement of dowel pin 186. During installation, the dowel pin 186 is pushed completely inside to secure the wristband. Once installed, there is no way to pull the dowel out thereby rendering the device tamper resistant. The silicone inserts 162 may align with the through hole in the arms to allow the dowel pin 186 to go through and provide added stability. During a typical installation, the hollow tube is inserted into the anchor points (both big and small wrist anchors) in-house. The device and wristband are then ready to ship to a customer. At the customer site, based on the client's wrist the wristband is attached to an anchor point (big anchor 182 if big wrist; small anchor 180 if small wrist. If small wrist, the excess band to the left of anchor point 180 is cut and discarded). Then the client's wrist size is measured at the other end 176 and then the wristband is cut along the serrated edge to match the size measured size. The hollow tube is inserted into the last/final hole closest to the cut edge. The wristband with the attached device is wrapped around the wrist and held in place. The dowel pin is inserted into the final hole where the hollow tube is thereby completing the installation.

Figure 23:
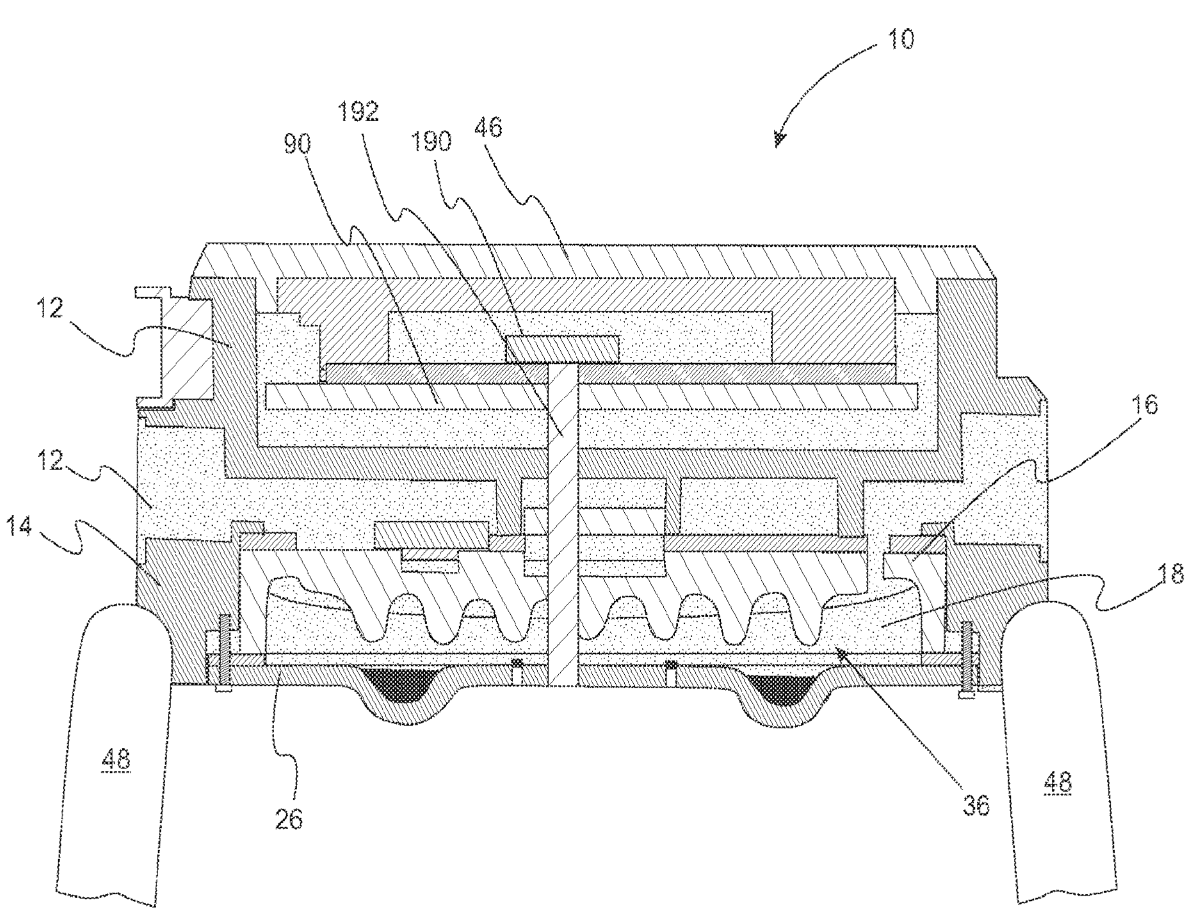
FIG. 23 shows interior and top views of the primary PCB and polycarbonate rod of the device according to one or more embodiments.
Figure 24:
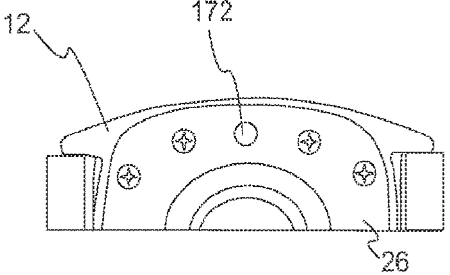
FIG. 24 shows a bottom view of polycarbonate rod at the bottom of the wrist piece.

FIGS. 23 and 24 illustrate tamper resistance features of the device. On the bottom of the primary PCB 110 for each side, 90 degrees from the wrist strap attachment, an IR emitter and collector 190 (i.e., an IR sensor) is provided. The module can also have an ambient light collector/sensor The IR is guided through an infrared-transparent rod 192 (e.g., polycarbonate rod) to the wearer's skin. The IR transparent rod in optical communication with the IR sensor and the first face of the wrist piece. The reflected signal is monitored for interference or reduction. If a solid material (e.g., business card) is inserted between the skin and the ethanol collection area, the beam path will be broken, and this action will be recorded. The change in the reflected IR signal indicates tampering. This signal may be paired with the change in the ambient light signal (which monitors if the unit is lifted or removed) and the change in humidity/temperature sensor reading to confirm tamper.

Figure 25A:
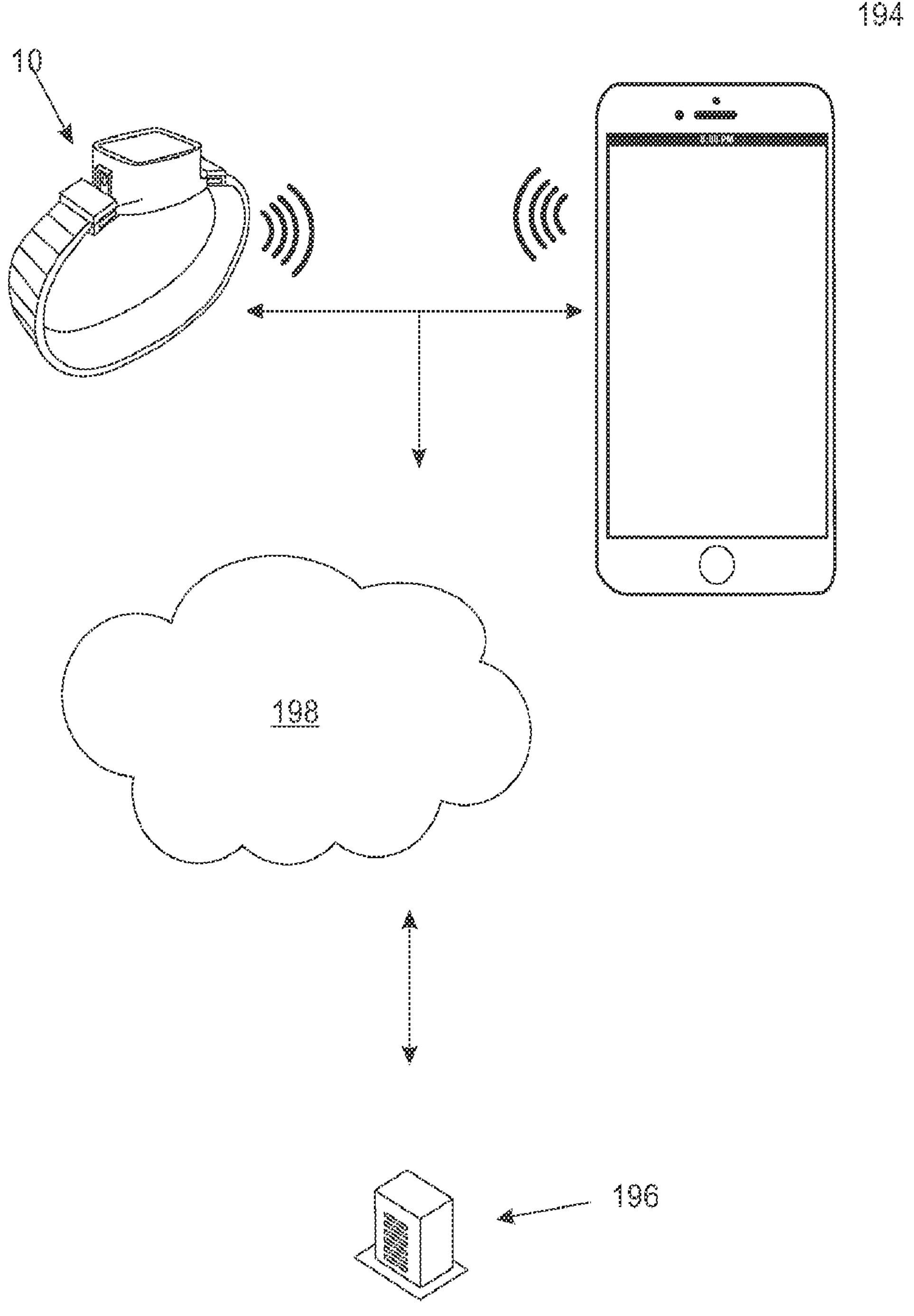
FIG. 25A show an alcohol monitoring system for monitoring alcohol consumption using the device of FIG. 1.
Figure 25B:
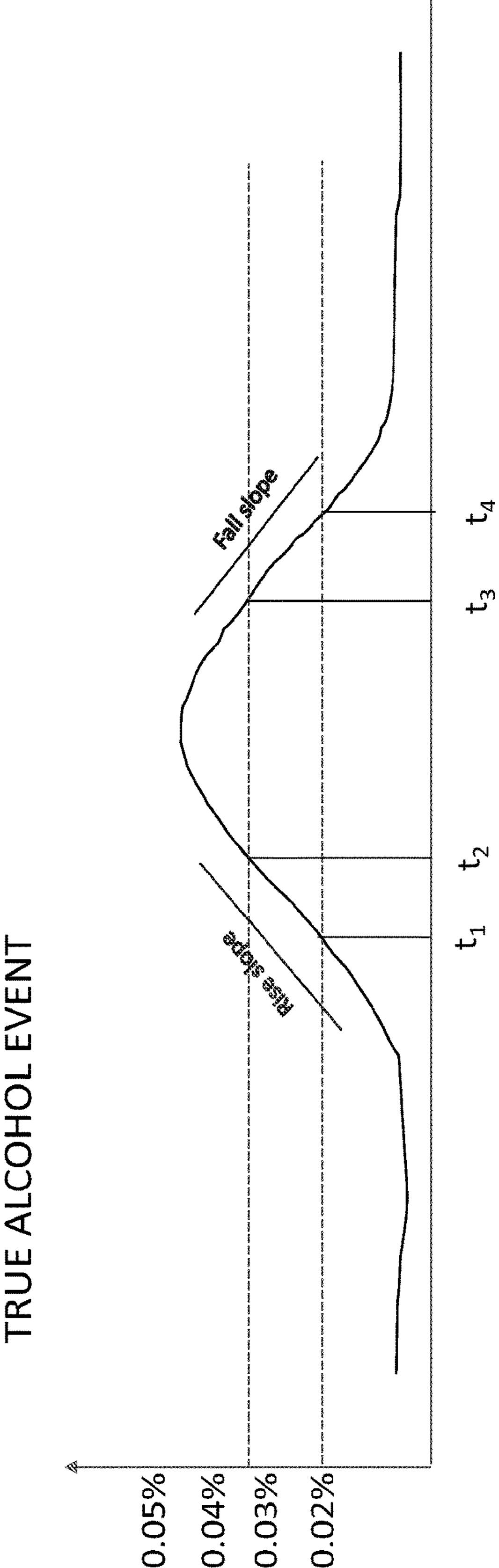
FIG. 25B provides a plot and related analysis for a true alcohol event.
Figure 25C:
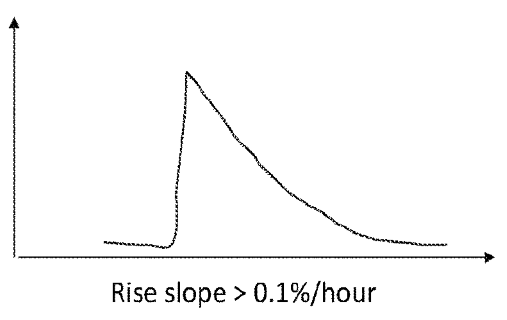
FIGS. 25C, 25D, 25E, and 25F provide plots and related analysis for a false alcohol event.
Figure 25D:
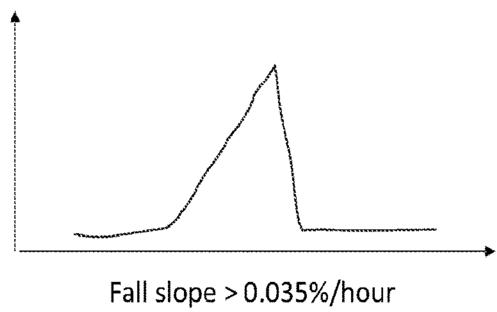
Figure 25E:
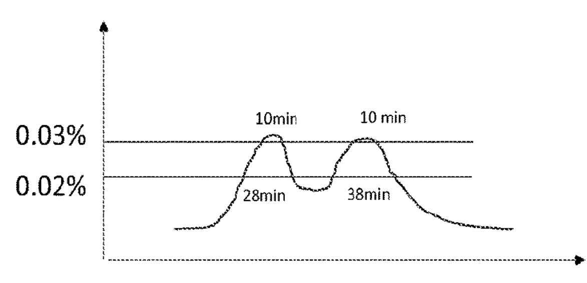
Figure 25F:
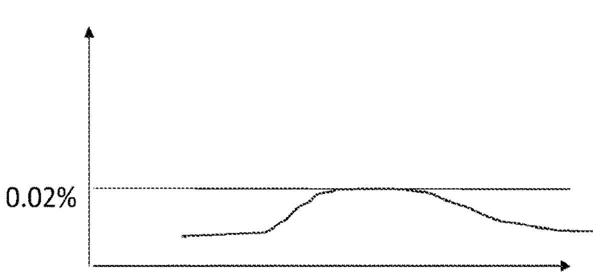

Referring to FIGS. 25A-F, a schematic of an alcohol monitoring system using wrist-worn device 10 of FIGS. 1 to 24 and plots related to peak analysis are provided. The control circuitry 42 in wrist-worn device 10 is configured to communicate with one or more computing devices 194, 196. The computing device can be a smartphone, tablet, or a computer. Wrist-worn device 10 can communicate with the computing devices through wireless connections or wired connections. In a refinement, the communication can be over the Internet or other cloud networks. In a variation, the one or more computing devices 194, 196 and/or control circuitry 42 is configured to receive a plurality of alcohol measurements as a function of time over a first predetermined time interval to provide a time-dependent alcohol concentration plot. In a refinement, the one or more computing devices 194, 196 and/or control circuitry 42 is configured to apply smoothening and/or filtering to the time-dependent alcohol concentration plot. For example, the filtering operation can be a FFT filter, percentile filter, and the like. In a further refinement, the one or more computing devices 194, 196 and/or control circuitry 42 is configured to apply a baseline correction algorithm to the time-dependent alcohol concentration plot. For example, the baseline correction algorithm can be a rubberband baseline correction algorithm, an ALS baseline correction, and the like. In a further refinement, the control circuitry is configured to apply a humidity correction factor and a temperature correction factor. In still a further refinement as depicted in FIGS. 25B, 25C, 25D, 25E, and 25F, the one or more computing devices 194, 196 and/or control circuitry 42 is configured to evaluate peaks in the time dependent alcohol concentration plot by determining a first slope for a rise in alcohol concentration and a second slope for an associate fall in alcohol concentration. In still a further refinement, one or more computing devices 194, 196 and/or control circuitry 42 is configured to determine that a peak in the time-dependent alcohol concentration is positive for alcohol consumption if the peak extends from the baseline by a predetermined amount for at least a predetermined duration and if the first slope and second slope are less than a predetermined rising slope and a predetermined falling slope, respectively. In a refinement, the predetermined amount is a TAC (i.e. or corresponding signal) of at least 0.01%, 0.015%, 0.02%, 0.025%, 0.03%, 0.04%, or any desired percent. In some refinements, the predetermined rising slope and the predetermined falling slope are each independently at least 0.05%/hour, 0.1%/hour, 0.15%/hour, 0.2%/hour, or 0.2%/hour. Typically, the predetermined rising slope and the predetermined falling slope are independently at most 0.7%/hour. 0.5%/hour, 0.45%/hour, 0.4%/hour, or 0.3%/hour. For example, FIG. 25B provides a peak that corresponds to a true alcohol event. In this example, the peak exceeds the baseline by more than a predetermined value of 0.02% (i.e., a signal that corresponds to TAC of 0.02%). The peak above 0.02% continuously for 1 hour (i.e., a first predetermined duration. The peak above 0.03% continuously for 30 min (i.e., a second predetermined duration.) The rising slope is less than 0.1%/hour (i.e., the predetermined rising slope) and the falling slope is less than 0.035%/hour (i.e., the predetermined falling slope). FIGS. 25C-F provides peaks that do not represent true alcohol events.

A similar set of analysis can be carried out for tamper detection based on change of values of the various tamper sensors i.e., IR sensors, ambient sensors, humidity and temperature sensors, and strap tamper bit. The tamper analysis involves:

1. Tamper is detected in the software algorithm by analyzing data from IR sensors 1 & 2, Humidity and Temperature 1 & 2, alcohol sensor, and strap tamper bit.
2. For IR sensors 1 and 2, the raw data is filtered and then baseline corrected like peak analysis method (i.e., FFT filtering and rubberband/ALS baseline correction). Next, the average value of IR sensor over a 30-minute interval (6 data points at 5 min/data point) is computed and compared to the average of the past TEN 30-minute intervals (60 data points at 5 min/data point). If the delta change is greater than or equal to 30%, the event is flagged as a tamper event. The start of tamper event is the start of the 30-min interval and end is computed as when a subsequent 30-min interval is back to within 10% of the initial average of the past TEN 30-minute intervals.
3. A.) For relative humidity signal-based tamper detection, the software algorithm checks if the average value of humidity sensor 1 (facing the skin) over a 30-min interval is below 40% RH indicating unit off the skin or above 100% indicating submersion or leak. For humidity sensor 2 (facing the vent above the sensor), the algorithm checks if the average value over a 30-min interval is above 100% indicated submersion.
   B.) For humidity sensors 1 and 2, the algorithm also computes sudden spikes where the change in humidity (average of 30-min of data compared to previous FIVE 30-min interval) is above 15% indicating possible tamper e.g., via a skin seal issue, steam guard tamper, possible insertion to block wristpiece, or unit removed from skin.
4. A.) For temperature signal-based tamper detection, the software algorithm checks if the average value of temperature sensor 1 (facing the skin) over a 30-min interval is below 20 C indicating unit off the skin or above 40 C indicating unusual activity. For temperature sensor 2 (facing the vent above the sensor), the algorithm checks if the average value over a 30-min interval is below 20 C or above 40 C indicating an extreme climate exposure.
   B.) For temperature sensors 1 and 2, the algorithm also computes sudden spikes where the change in temperature (average of 30-min of data compared to previous FIVE 30-min interval) is above 5 C indicating possible tamper e.g., via a skin seal issue, unit removed from skin, or unusual activity.
5. For relative humidity sensors, temperature sensors and the alcohol sensor reading, the software algorithm also keeps track of standard deviation of the RAW signals i.e., noise in data and triggers a tamper event if the standard deviation in a 1-hour window falls below a threshold indicating that the signal has very low noise i.e., unit is witnessing a very stable environment that is not representative of skin conditions.
6. For strap tamper analysis, the algorithm keeps track of the tamper bit which is set to 0 (LOW or FALSE) if the strap is secure and 1 (HIGH or TRUE) if strap is cut.
7. Note: In the above implementations
   a. the time intervals of 30-minutes is adjustable
   b. the comparison time interval is adjustable i.e., could be previous ONE 30-minute interval, FIVE 30-minute interval, or TEN 30-minute interval.
   c. The event may be marked a tamper event only if such an event continues for more than 1 hour. This time is also adjustable.
   d. The values that determine tamper (delta change or % change) are also adjustable.
   e. Tamper events from multiple sensors can be overlaid to increase confidence of detecting a tamper event. E.g., if all three of the following happen at the same start time and continue for the same duration then the confidence level of a tamper event indicating unit taken off the skin is HIGH:
      i. the standard deviations of alcohol sensor, RH sensors, and temperature sensors all fall below threshold
      ii. humidity sensor RH1 falls below 40% RH
      iii. temperature sensor T1 falls below 20 C Similar to the peak analysis plot, a plot for the tamper analysis is generated where all the tamper events are highlighted (start to end) for each sensor on a time-series plot In another implementation, the peaks for alcohol analysis and events for tamper analysis can be reported in tabular form where the table indicates:

1. Detected alcohol peaks with
   a. start time, end time, duration, peak value, rise slope, fall slope, threshold criteria, peak qualification criteria
   b. peak qualification criteria can have an ID assigned e.g., ID 1=confirmed alcohol consumption, ID 2=possible alcohol consumption and so on.
2. Detected tamper events with
   a. start time, end time, duration, average value, delta change, tamper qualification criteria
   b. tamper qualification criteria can have an ID assigned e.g., ID 1=IR1 tamper, ID 2=IR 2 tamper, ID 3=RH 1 below 40% RH, ID 4=RH 1 above 100% RH and so on.

Figure 26:
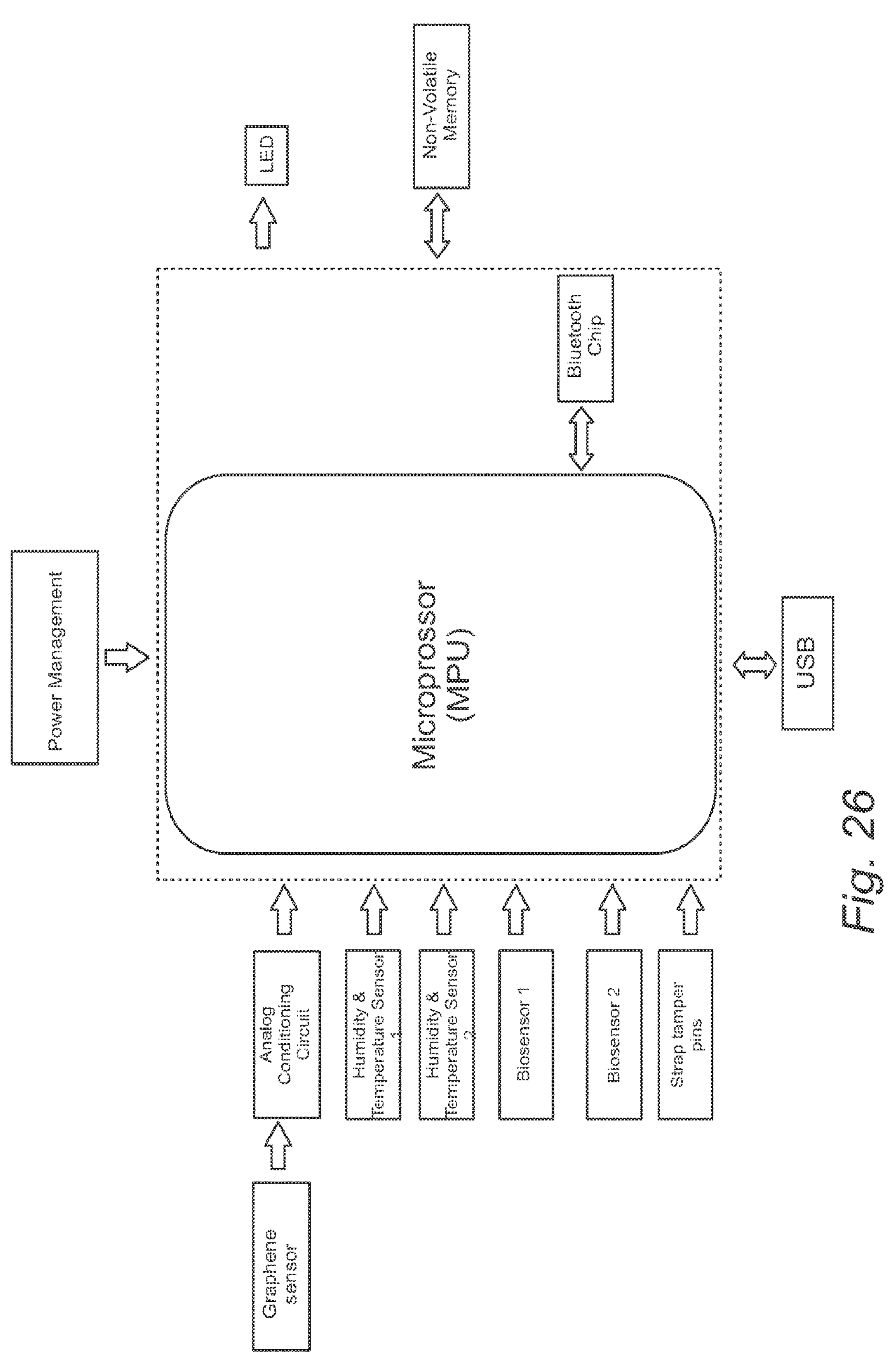
FIG. 26 is a schematic representation of electronic hardware in the device according to one or more embodiments.

FIG. 26 schematically illustrates the electronic hardware inside the device. The actual implementation of the hardware inside the device is split up into two boards: primary (main) PCB and daughter PCB. The main components of the hardware are shown in the table below:

| | Main Components | Placement | Role |
|---|---|---|---|
| 1 | Microprocessor | Main PCB | Control overall operation of the device |
| 2 | Power Management Unit | Main PCB | Battery management |
| 3 | LED | Main PCB | Status Indicator |
| 4 | Graphene Sensor | Daughter PCB | |
| 5 | Analog Conditioning Circuit | Main PCB | Amplify and Filter alcohol sensor signal |
| 6A | Humidity & Temperature 1 | Daughter PCB | Measures Humidity & Temperature below the sensor (facing skin) |
| 6B | Humidity & Temperature 2 | Daughter PCB | Measures Humidity & Temperature above the sensor (facing vent 80) |
| 7 | Biosensor 1 | Main PCB | Measures IR and Ambient light signal |
| 8 | Biosensor 2 | Main PCB | Measures IR and Ambient light signal |
| 9 | Non-volatile memory | Main PCB | Stores measured data |

-continued

| | Main Components | Placement | Role |
|---|---|---|---|
| 10 | Bluetooth module/chip | Main PCB | Receive and transmit data |
| 11 | USB | Main PCB | Program, charge, and memory-read |
| 12 | Strap tamper line connection | Main PCB | Indicates if strap has been cut |

Microprocessor: The microprocessor controls the operation of the entire device. The high-level functionality may include: 1) Reading all the data from the various sensors, including the custom graphene sensor, biosensors 1 and 2, temperature/humidity sensor 1 and 2, and the tamper pin; 2) Maintaining the time stamp on collected data using a programmed timekeeper chip or an internal real-time counter; 3) Storing the data from the sensors to internal non-volatile memory along with the timestamp; 4) Transferring this data to the phone (app) via Bluetooth Low Energy, as well as over USB; 5) Processing of the various characteristic commands sent from the phone (app) via Bluetooth; 6) Keeping the system in the lowest possible power mode possible to achieve functionality and required battery life.

Power management unit: This includes hardware for battery management, which may include: 1) A connector to a rechargeable Li—Po battery; 2) Charge management circuit for USB charging, over-charge and over-discharge protection; 3) Voltage regulator to provide stable Voltage for MPU operation and supplying power to digital sensors hardware operation; 4) Circuit to provide 1V bias to custom graphene sensor; 5) Reading battery level.

LED: The LED indicates the status of the hardware/unit for: 1) Battery charging when USB plugged in (e.g., solid RED when plugged in); 2) Advertisement Mode Flashes (e.g., blinking RED); 3) Bluetooth Data transfer (e.g., blinking GREEN); 4) Low charge (e.g., solid RED).

Graphene sensor: Custom alcohol sensor as described in U.S. Pat. No. 10,845,324 and U.S. Patent Application Publication No. 2020/0373598, the disclosures of which are incorporated by reference herein in their entirety. The custom graphene sensor is an analog sensor which operates at a constant bias of 1V (that is provided through the power management circuit). The 1V bias can be applied or removed through a switch which is controlled by the MPU. A command can be sent to the MPU to activate/deactivate this switch. In alternative embodiments, the sensor may be configured to operate at other bias voltages e.g. 100 mV. As mentioned above, in alternative embodiments, the sensor may be configured to detect a biochemical substance other than ethanol.

Analog Conditioning Circuit: This circuit includes a transimpedance amplifier and a filter. The transimpedance amplifier amplifies, buffers, and converts the raw custom graphene sensor signal (which is an analog current signal) and to an analog voltage signal. The amplification or gain factors which may be available are, for example, 0.9 Mohm, 1 Mohm, 5 Mohm, 10 Mohm. In alternative embodiments, the gain factors can be different e.g., 0.32 Mohm, 0.45 Mohm, 0.9 Mohm, 5 Mohm. The gain factor may be selected through a set of switches which are controlled by the MPU. A command can be sent to the MPU via phone app to select the desired gain. The amplified signal is filtered through a low-pass filter to remove high frequency noise. The final output of the Analog Conditioning circuit is sent to the MPU. The MPU has an internal 10-bit Analog to Digital Convertor (ADC) which converts the analog voltage from the conditioning circuit to a digital value.

Humidity and Temperature sensors: The humidity and temperature sensors 1 and 2 measure the relative humidity, such as in the range 0-100% RH and temperature in the range −40-+125 C. The output of the sensor module is digital and is directly read by the MPU through the I2C interface.

Biosensors: Biosensor 1 and 2 are fully integrated, 16-bit infrared and ambient light sensor. In one or more embodiments, the unit has an infrared emitter in the package and one ambient light photodiode and one infrared photodiode. The communication interface is I2C. This sensor may be used to detect tampering where a foreign material is used to block the access of vapors from the skin to the unit. The biosensor can be used for advanced monitoring of health as well (e.g., pulse oximetry).

Non-volatile memory: The main board has an EEPROM to store the timestamped collected data from the sensors. The data is read/written by the MPU through the I2C interface. In one or more embodiments, the hardware and firmware allows 30 days of sensor data to be stored. The EEPROM size can be increased to allow for more than 30 days of data to be stored.

Bluetooth chip: The main board includes a Bluetooth Low Energy (v5) module that has an integrated Bluetooth software stack and a shielded regulatory certified version with built-in antenna. Data collected by all the sensors is transmitted to the external world (phone app) by the Bluetooth module. The module is interfaced via UART for serial data applications. The Bluetooth module can be kept in the active state or dormant state which can be controlled by the MPU. The Bluetooth chip and the microprocessor can be a single integrated system-on-chip module as well. Bluetooth is just one method to transmit data collected by the Hardware Unit to the external world. Other technologies may be used as well (e.g., NFC, WIFI, cellular, satellite etc.).

USB unit: The interface on the board can be used to charge the battery on board, program/flash the microprocessor firmware, and read the non-volatile memory. The USB is interfaced with a chip to facilitate USB to serial UART data transfer.

Strap tamper line: In one or more embodiments, the main board has two pins for connecting to the metal wires running through the strap. If the strap is cut (tampering), the connection between the two pins is broken and the MPU reads it as a 'HIGH' indicating tamper.

The field operation of the module requires collection of the sensor data (custom graphene sensor, humidity and temperature sensor 1, humidity and temperature sensor 2, biosensor 1, biosensor 2, strap tamper bit) continuously for multiple days of wear. In one or more embodiments, the sensor data may be collected every 5 minutes and run for 28+ days, although these time frames are not intended to be limiting. The collected sensor data is stored in the memory along with the timestamp of when the data was collected. This stored data is uploaded to an external device (phone) via Bluetooth periodically (e.g., every 6 hours).

According to one non-limiting embodiment, the sequence of steps for setup of the Hardware Unit (HWU) for field operation is described below. Step 1: Flash the MPU with the operating Firmware (from a computer) via the USB or over-the-air (OTA) via Bluetooth. This also resets the unit and initializes all the MPU peripherals, biosensors, and the BLE module. While the USB is plugged in, the MPU is in idle mode and can be sent messages/commands via the USB using the computer terminal or via Bluetooth using a phone app.

The USB commands include checking connection, reading EEPROM data, setting PIN number for Bluetooth bonding, and setting the timestamp on the MPU. Using the phone, the commands that can be sent over Bluetooth are connect, disconnect, stop all measurements, set time on the MPU, setting timer for livestream mode and starting the livestream mode, sending unit into and out of PowerDown mode, turning the 1V bias across the sensor On or Off, sending the unit into Record mode, setting the advertisement mode parameters, reading the full EEPROM memory, erasing the full EEPROM memory, controlling the gain resistance in the analog conditioning circuit. Many of these commands (over USB or Bluetooth) are only for ADMIN mode troubleshooting. Once the USB is unplugged, the HWU goes into a PowerDown mode where the Bluetooth chip is in dormant state and the HWU can no longer communicate with the phone app.

Step 2: Setup the PIN using the USB command interface. This step is done through custom software and GUI. Step 3: Establish a Bluetooth connection between the phone and the HWU. Next, bond and pair the unit to one phone using the PIN in Step 2. This set of controls is through the custom phone app over Bluetooth. Step 4: Set time on the MPU using the app to note the starting timepoint of data collection. This step can be done during Step 2 via USB also using the custom software. Step 5: Turn ON the custom graphene sensor from the app. This command asks the MPU to turn the switch to apply 1V bias across the custom graphene sensor. Step 6: Turn ON PowerDown mode from the app. This command asks the MPU to initiate the PowerDown mode. The PowerDown command ensures that as soon as USB is unplugged, the unit goes into PowerDown where it consumes low power.

Step 7: Set RECORD mode from the app. This command sends the HWU in the data record mode for field operation. The command has 3 parameters: data acquisition time (i.e., how often is data collected from the sensors and stored into the memory); BLE upload time (i.e., how often the stored data in the memory is sent via Bluetooth to the phone); BLE timeout (i.e., how long will the HWU be awake to establish connection with the phone to send data before going back to low power mode).

In one or more embodiments, the standard REC mode parameters are 5 min, 6 hours, and 240 secs. That is, data is recorded from the sensors and saved to the memory every 5 minutes, the unit wakes up every 6 hours and sends the entire 6 hours-worth of data (i.e., 72 data points) over Bluetooth to the phone, and the unit is awake for 240 secs at the 6th hour mark trying to establish a Bluetooth connection with the phone. If the connection is not established, the unit will try again after 6 hours and, if connected, transmit all data since the last established connection (i.e., 144 points), and so on. Of course, it is understood that these time intervals are merely exemplary, and not intended to be limiting.

Step 8: Disconnect the BLE connection in the phone app once the RECORD mode is initiated. Step 9: Unplug USB to enable PowerDown mode. The HWU is now in Record mode and in the lowest power consumption state.

In one or more embodiments, the firmware has a force disconnect function which kills a live Bluetooth connection if no Bluetooth activity is happening for a set period of time e.g., 1 minute. In such a situation, to conserve battery the firmware will force disconnect and kill the Bluetooth connection.

Step 10: Admin Mode connection during REC mode operation in the field. There may be instances where an administrator would like to connect to the HWU and troubleshoot in the field (e.g., read all the data in the memory on the spot). To facilitate this, the HWU has an advertisement mode (ADV) where the unit wakes up every nth minute (where n can be set by the administrator) and has the Bluetooth in the active state for a set time window (also programmable by the administrator). After the set time window is over, the unit goes back into the lowest power down mode. This ADV mode may be indicated by LED flashes. During the ADV mode, the phone app can be used to connect to the HWU and perform admin mode operations. The admin mode operations may require password verification.

Figure 27:
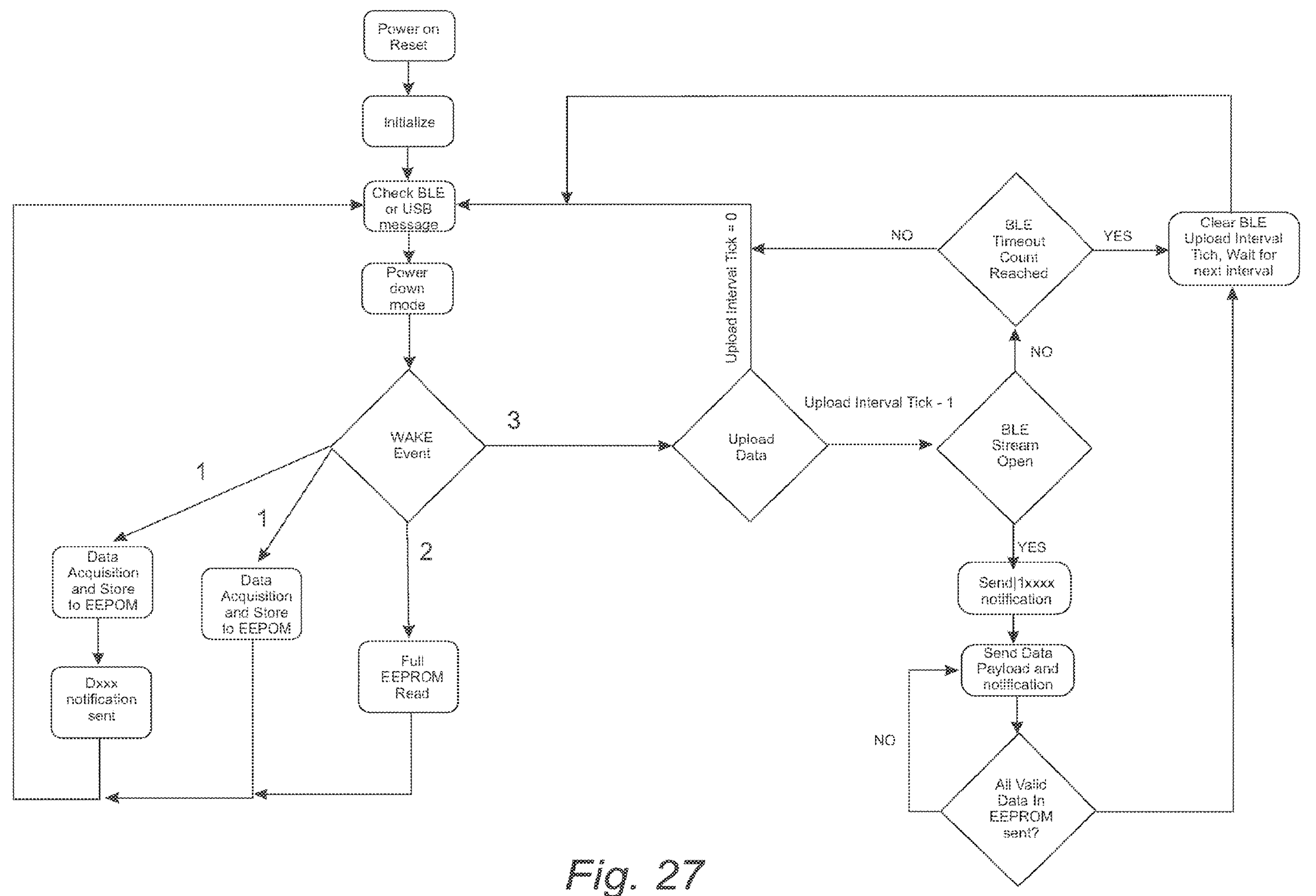
FIG. 27 is an operation flowchart for the device according to one or more embodiments.

The high-level operation of the HWU in the field according to one or more embodiments is illustrated in FIG. 27. The HWU can run in LIVESTREAM Mode or RECORD Mode. The LIVESTREAM mode is not used in the field and is only for internal testing. LIVESTREAM mode allows real time data collection at a set interval (which can be programmed) and immediate transmission to the phone via Bluetooth. This allows access to data in real time. In the field, the unit will be running in the RECORD Mode. The use of LIVESTREAM Mode may be limited to quick confirmation checks before setting up RECORD Mode.

When the HWU is powered on, in the initial state, the MPU initializes all peripherals, the two biosensors, and the Bluetooth (BLE) module. The MPU will then check the UART buffers of the Bluetooth and USB interfaces to check for new data/commands that will be processed and acted upon.

There are two main types of BLE messages that can be received by the HWU: 1) BLE module status messages: These messages include Connect, Disconnect, Stream Open, etc.; 2) Write Characteristic Data: These are the actual BLE commands that are received from the mobile application. The MPU is expecting 5 bytes for write characteristic data/BLE commands. This state will also check for any USB commands coming across the UART. USB commands will be initiated by the GUI software.

Once the RECORD mode is started, the unit is in PowerDown. In this mode, only the Periodic Interrupt Timer interrupt (which handles the timing for Livestream, Record, and BLE upload events) will wake up the MPU or the Peripheral UART will wake up the MPU. Active mode: Active mode is usual operation with no PowerDown. Dormant mode: Dormant mode is the maximum power savings with much of the module disabled.

The MPU unit has 3 sleep modes: Idle, Standby, and PowerDown. The BLE module can operate in Active Mode (usual operation with no PowerDown) or Dormant mode (where maximum power saving is achieved as much of the module is disabled).

The HWU has 2 PowerDown modes for low power operation. PowerDown Mode 1: The MPU in the idle sleep mode and the BLE module in active mode. The only other chip capable of power savings mode is the biosensor, which automatically enters a standby mode when not taking measurements. When the MCU is in idle sleep mode, any interrupt will wake the device. Idle sleep mode does not affect the functionality of the device. This mode is used for testing and for setting up the device. When the USB is connected, the device is in Power Down Mode 1.

PowerDown Mode 2: The MPU is in PowerDown sleep mode, which is the best sleep mode and consumes the least amount of power. The BLE module will be in dormant mode, which is the best power savings mode. The biosensors will be in standby mode. This mode is set by the powerdown command via the app.

When the MPU is in PowerDown sleep mode, the only interrupt sources that will wake the device are pin change interrupts and PIT (Periodic Interrupt Timer). Also, the timers that control the live stream tick, recording tick, and BLE upload tick will wake the MPU.

The MPU controls when to put the BLE module in dormant mode, and when to wake it up. The BLE module will be in dormant mode until the BLE upload interval tick interrupt occurs, at which time the MPU will wake the BLE module and put the device into PowerDown Mode 1. It will stay in PowerDown Mode 1 until all the data has been sent via Bluetooth or an upload timeout has occurred. PowerDown Mode 2 has a significant effect on the functionality of the device. Since the BLE module is in dormant mode, no BLE communication can occur. This PowerDown mode is used for the RECORD mode, where the device will only wake for uploading data over BLE or periodic advertising.

PowerDown operation in the field according to one or more embodiments is described below:

1) Device is plugged into USB to fully charge: The mobile app can communicate to the device to via Bluetooth. The app can then be used to send the command to put the device into recording mode. Once a recording is started, the Bluetooth connection on the app is closed and the USB cable is unplugged, and the device goes into PowerDown Mode 2.
2) The mobile app knows the device will not be able to wake up and send data until the next BLE Upload interval. The mobile app will then be in a state where it will not try to scan for the device until the next BLE Upload Interval. After the time interval has occurred, the device will look for a connection to send data. The mobile app will also start scanning for the device. Once a connection is established, the device will send data to the mobile app. The device will then go back into PowerDown Mode 2 after all data is transferred and the mobile app disconnects. The BLE Upload Timeout interval allows time for the device and app to reestablish a connection. Second, if the connection is not established within the timeframe, it will go back into PowerDown Mode 2 and wait for the next BLE Upload Interval.

The value for the recording time corresponds to the "DAQ Measurement Interval" in the RECORD 'R' command. When the interrupt for data recording happens, it is time to take measurements from the sensors and store to the EEPROM. Data measurements are taken from the custom graphene sensor (converted to digital by ADC), temperature and humidity sensors (I2C), two bio sensors (I2C), and battery level (converted to digital by ADC). At the beginning of this state, the current timestamp is also read. After the data and timestamp have been acquired, they are stored to EEPROM. During data acquisition, the device starts filling up the EEPROM at sequentially higher addresses. It will keep incrementing the write pointer until the EEPROM is full or an EEPROM erase command is sent. Reading data from EEPROM and sending data over BLE does not affect the EEPROM write pointer. The EEPROM read pointer will increment after each data set is sent over BLE. The "tamper" bit indicator is also written to EEPROM, but its value is generated by a separate interrupt service routine that fires when the "tamper" pin changes.

The timer value that generates the BLE upload interval tick is set by the last two bytes in the 'R' command sent by the mobile application. When the interrupt for the BLE upload interval occurs, it sets the 'BLE upload tick' variable and that will not get cleared unless data is sent or it times out.

First, the unit checks to see if there is an active connection to the mobile phone via BLE and the data stream is open. If there is a stream open, it will move to the next state on receipt of a read flash memory command. Once the app sends this read notification, the unit sends the data payload. Each recorded data point is sent with 2 notifications with half the data in each notification. The firmware will loop until all the data has been sent since the last BLE upload event. Once all the data is uploaded, the 'BLE upload tick' variable is cleared and then unit goes back to PowerDown mode.

The BLE Upload Timeout count is set by the last value in the R command. This value is the number of seconds that the device tries to establish a BLE connection to the mobile phone for data upload (used in record mode). If a timeout occurs, then the data that was scheduled to be sent in that interval will be added to the data at the next interval. This state checks to see if the timeout value has been reached. A special one second tick is used to look for a BLE connection until the count has expired. If a timeout has occurred, it will proceed to the "Clear BLE Upload, Wait for Next Interval Tick" state. Here, "BLE Upload Tick" variable is reset, and the unit goes back into PowerDown mode.

The BLE Upload Timeout function is designed for power conservation. If no connection occurs, the device will go back into power down mode and attempt communication at the next upload interval. There are other embodiments to achieve Bluetooth data transmission. For example, the MPU and Bluetooth chip can be configured to be always in a low power advertisement state waiting for the phone app to request data. In this embodiment, it is the phone app that keeps track of time and can connect anytime in the low power advertisement ping and request data and then the unit wakes up to transmit relevant data. This mode is different as unit never goes to deep powerdown mode. Also this means higher battery consumption.

Full Flash/EEPROM Read: This state will send all valid data acquisition data sets in EEPROM over BLE or USB.

a) BLE full EEPROM read—The periodic advertisement mode allows on-demand data upload from the device if the administrator wants to get data outside of the BLE upload intervals. Once a connection is made during the advertisement mode, a read full flash command can be sent from the app to download the full EEPROM data. After the data is read, the app can be disconnected and the device will go back into Power Down Mode 2
b) USB Full EEPROM read—The USB upload command is generated by the GUI software. The USB upload command is mainly used for testing, and for downloading data when the BLE stream is unavailable. If the USB upload command has been received, the firmware will loop until all the data has been sent over USB. The format that the data is sent over USB is the same as the data format sent over BLE.

Data Payload Layout: 1) In EEPROM: The initial address in the memory location are the configuration bytes. The data from the HWU along with the timestamp is stored sequentially starting at address 0x100 in the memory. 2) Data payload sent from EEPROM to the phone app: The data payload sent from the HWU to the phone during a BLE upload command or a full EEPROM read command includes two notifications for each data point. Each notification contains part of the data and the last 4 bytes of each notification contain descriptors.

The data includes raw binary values (in HEX format) for the sensors, battery, tamper pin and timestamp. These values are converted to respective numbers/values on the phone. For example, the Humidity_RAW and Temp_RAW value is converted the relative humidity level % RH and temperature° C. values using the conversion equations provided by the humidity/temperature chip manufacturer. The Arborsense_RAW is the custom graphene sensor output in voltage. Biosensor values (Ambient and Bio) are numerical values (counts). Battery value is converted to % Level using a calibrated equation. Tamper pin is just a flag where digital bit '0' is treated as 'No tamper' and '1' is treated as 'Tamper'.

The Livestream mode and Record mode are mutually exclusive, and the unit can only be run in one mode at a time. If the Livestream mode has been started from the mobile app and the livestream timer tick has occurred, the HWU will move to the "Data Acquisition and store to EEPROM" state (like RECORD mode). The HWU will also send the data to the phone immediately in real-time. The livestream timer tick is generated by the Periodic Interrupt Timer. The value for the livestream timer tick can be set by the user via the phone BLE command. If no value is sent to the device, a default value of 5 seconds is used.

Data Acquisition and Store to EEPROM. When the interrupt for data collection livestream timer tick happens, measurements are taken—from the custom graphene sensor (converted to digital by ADC), temperature and humidity sensors (I2C), two bio sensors (I2C), and battery level (converted to digital by ADC)—stored to the EEPROM, and also sent back the phone along with a notification. At the beginning of this data acquisition state, the current timestamp is also read. After data and timestamp have been acquired, they are stored to EEPROM. During data acquisition, the device starts filling up the EEPROM at sequentially higher addresses. It will keep incrementing the write pointer until the EEPROM is full or an EEPROM erase command is sent. Reading data from EEPROM and sending data over BLE does not affect the EEPROM write pointer. The EEPROM read pointer will increment after each data set is sent over BLE. The "tamper" bit indicator is also written to EEPROM, but its value is generated by a separate interrupt service routine that fires when the "tamper" pin changes.

Data Payload Layout in Livestream Mode. 1) In EEPROM: The layout of the data stored in the memory is identical as the RECORD mode. 2) Data payload sent from HWU to the phone in real-time: In Livestream mode, the data payload is sent from the HWU to the phone with a notification which contains all the data.

The data processing and analysis may happen fully at the backend or partially on the backend and partially on the Hardware Unit itself. The backend could be the phone, a desktop, or the cloud. In some use cases or markets, the preferred implementation is the cloud or a desktop which is not-accessible to the wearer. In embodiments disclosed herein, the data processing happens at the backend and on a desktop/laptop.

As described above with respect to the Hardware Unit operation, the raw data collected from all the sensors on board is stored in the EEPROM memory module and transmitted via Bluetooth to the phone during the REC mode Upload. The data payload from EEPROM to the phone app includes two notifications for each data point. Each notification contains part of the data and the last 4 bytes of each notification contain descriptors.

The data is in binary values (HEX format) for the custom graphene sensor, humidity/temperature sensors, biosensors 1 and 2, battery, tamper pin and timestamp.

The data received by the phone app is converted to respective numbers/values and stored in .csv file format. For example, the Humidity_RAW and Temp_RAW value is converted the relative humidity level % RH and temperature° C. values using the conversion equations provided by the humidity/temperature chip manufacturer. The Arborsense_RAW is the custom graphene sensor output in voltage. Biosensor values (Ambient and Bio) are numerical values (counts). Battery value is converted to % Level using a calibrated equation. Tamper pin is just a flag where digital bit '0' is treated as 'No tamper' and '1' is treated as 'Tamper'. In one or more embodiments, data is stored on the phone in .csv files with the column layout as shown below:

| Time stamp | Readable | Vapor Concentration (V) | Temperature 1 (C.) | Relativity Humidity 1 (% RH) | Temperature 2 (C.) | Relativity Humidity 2 (% RH) | Ambient Raw 1 |
|---|---|---|---|---|---|---|---|

| Bio Raw 1 | Ambient Raw 2 | Bio Raw 2 | Tamper Bit | Battery Level | Flash Timestamp | Raw |
|---|---|---|---|---|---|---|

Timestamp: Unix timestamp. Readable Date: Date and time when the Bluetooth upload to the phone happened. Vapor Concentration: Raw voltage values from the custom graphene sensor in Volts.

Temperature 1: Temperature read by temperature sensor facing the amplification chamber in Celsius.

Relative Humidity 1: Relative Humidity read by the humidity sensor facing the amplification chamber in % RH.

Temperature 2: Temperature read by temperature sensor facing the vent 80 in Celsius.

Relative Humidity 2: Relative Humidity read by the humidity sensor facing the vent 80 in % RH.

Ambient Raw 1: Ambient light sensor response from IR_Sensor_1 recorded as counts.

Bio Raw 1: IR sensor response from IR_Sensor_1 recorded as counts.

Ambient Raw 2: Ambient light sensor response from IR_Sensor_2 recorded as counts. Bio Raw 2: IR sensor response from IR_Sensor_2 recorded as counts.

Tamper Bit: Bit='1' indicates open circuit and flags if wrist strap is cut.

Battery Level: Battery % recorded for each data point. Flash Timestamp: Date and time when the actual data point was recorded.

Raw: Data packet for data point in base64 notation.

For each BLE data upload every 6th hour during the RECORD mode, a new .csv file is created. These .csv files are used by the data processing algorithm.

In the current implementation, the folder which contains the .csv files on the phone is synced to the cloud from which the data is downloaded onto a desktop/laptop for processing. Other implementations for data transfer and storage are possible/recommended based on field requirements. For example, data can be stored in the raw binary (HEX) format on the phone and not .csv files and converted into numerical values only during data processing to save storage space. In another implementation, raw binary (HEX) data can be uploaded to the cloud immediately as it is received on the phone and then erased from the phone to prevent tamper and/or free storage space. These implementations become more obvious with other data communication technologies especially cellular, satellite, or Wi-Fi where the phone as a conduit for data collection and transmission to backend is not required.

Figure 28:
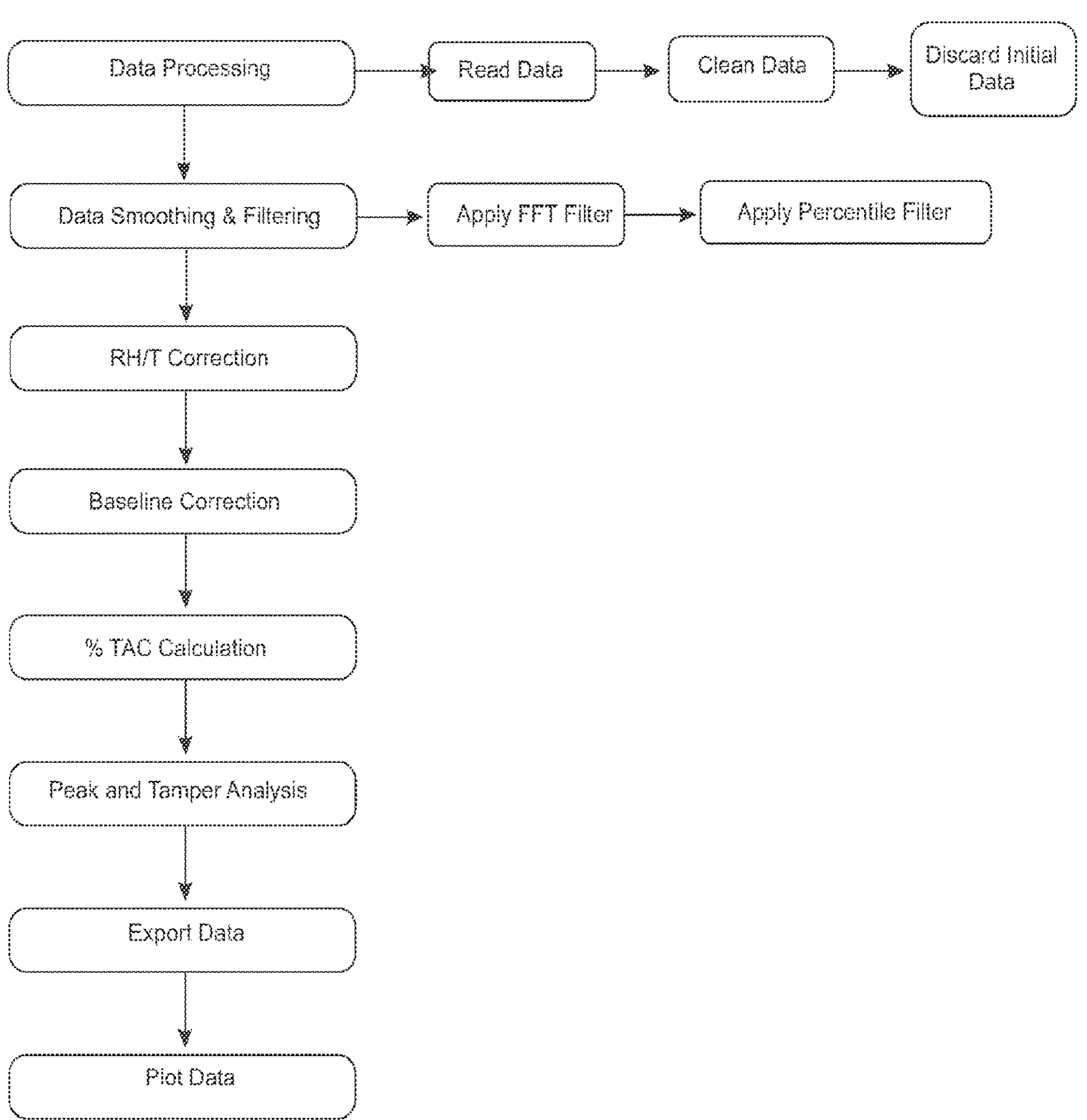
FIG. 28 is a flowchart illustrating software data processing and peak and tamper analysis in the device according to one or more embodiments.

The software data processing flowchart according to one or more embodiments is shown in FIG. 28. The .csv files generated from BLE upload in the RECORD mode are used as the input for data processing algorithm.

Read Data: The raw .csv files from the device uploads in the folder are appended into a single file which is used throughout the software to manipulate the data.

Clean Data: The Timestamp, Readable Date, and Raw columns are removed, and the Flash Timestamp column is set to the first column and renamed as Timestamp. The data is then sorted by these timestamp values. Lastly duplicate data is removed.

Discard Initial Data: If DISCARD_INITAL_DATA is set to true, the first row of data up until the specified DISCARD_INITAL_DATA_HOURS variable is removed from the dataset. The initial data to be discarded corresponds to the settling time of the custom sensor on the skin where it settles to skin humidity and skin temperature conditions.

Data Smoothening and Filtering: The raw data is smoothened by applying a FFT filter and a percentile filter to Vapor Concentration (V), Temperature (C), and Relative Humidity (% RH) columns. The filters removes any high frequency noise in the data signal and any sudden spikes caused by vibration or shock. The filters are also applied to the Bio Raw (counts) columns.

Apply FFT Filter: The FFT_POINTS_OF_WINDOW_VAL specifies the points of window which determines the cutoff frequency for the filter. The FFT_FILTER_APPLY replaces the original data with the FFT filtered data for use in further calculations. If set to FALSE, the original data is retained and a new column with the percentile filtered data is added to the dataset. The raw data then will be used in further calculations.

Apply Percentile Filter: The PERCENTILE_FILTER_VAL specifies the percentile value to filter on and the PERCENTILE_FILTER_WINDOW specifies the moving window in which the percentiles are computed. The PERCENTILE_FILTER_APPLY replaces the original data with the percentile filtered data for use in further calculations. If set to FALSE, the original data is retained and will be used in further calculations.

RH/T Correction: The vapor concentration values are corrected in accordance with temperature and relative humidity values. The temperature correction is applied on individual chunks of N-day data where N can be set by the administrator. In each N-day chunk, a correction factor is used for every humidity range in increments of 5% RH. In current embodiment these correction factors (for each humidity range within each N-day chunk) are calculated from real world dataset collected during device wear. In another embodiment, the correction factors may be universal.

In the current embodiment, the humidity (RH) correction, is split into two linear regimes with different correction factors. The RH_SYNTHESIS_THRESHOLD marks the cutoff humidity value which separates the two regimes and hence, requires different correction factors. After RH correction, the VC Corrected Synthesis column is created to merge the two corrected regimes on each side of the RH_SYNTHESIS_THRESHOLD value.

Baseline Correction: A baseline correction is applied to the VC Corrected Synthesis values to account for any signal drift in the sensor. In the present embodiment, a modified rubberband correction method is used. In another embodiment, a ALS baseline correction method is used. The correction is applied to the entire curve. A small amount of smoothing may be applied to the corrected signal e.g., using a Savitzky-Golay filter. The algorithm has built-in options of other baseline correction techniques which are currently disabled and can be used if needed. The baseline correction method is also applied to the filtered Bio Raw values.

% TAC Calculation: The baseline corrected vapor concentration values are multiplied by two conversion factors to compute the final transdermal alcohol concentration reading. These values are stored in column % TAC. The first conversion factor is computed for each custom graphene sensor based on benchtop electrical testing and represents the sensitivity of the custom graphene sensor to alcohol vapors. This factor accounts for the differences in sensor-to-sensor variation. The second conversion factor accounts for the device's sensitivity to the location where it is placed (wrist vs. ankle).

Peak Analysis: Peak analysis is performed on the % TAC values to isolate alcohol events. Each event is determined by a required peak height (height from baseline), peak prominence (height from curve), duration above 0.02%, duration above 0.03%, TAC absorption slope, TAC elimination slope, and area under the curve (AUC). For each peak event that meets the MIN_PEAK_HEIGHT and MIN_PEAK_PROMINENCE requirement, each of the above parameters are computed on the event and stored in a new file.

Tamper Analysis: Tamper analysis is performed on the filtered and baseline corrected Bio Raw values to determine tamper events. Each event is determined by a signal change (from baseline), a minimum required signal change (from baseline), and duration above 1. For each peak event that meets the MIN_SIGNAL CHANGE and DURATION requirement, each of the above parameters are computed on the event and stored in a new file. In other embodiments, similar criteria can be applied the humidity and temperature sensor values to compute and store events that qualify as tamper events.

Export Data: The files containing all the raw data and calculations is exported in .csv file format. A second .csv is exported containing a list of the alcohol event data and associated metric data from Peak Analysis.

Plot Data: A report is generated with the timeseries plot exported in readable format (e.g., pdf) containing the raw data, baseline corrected signals, peak events, IR sensors, ambient sensors, tamper bit, and device battery level. The algorithm provides the option to generate the report over a selected day and time range. The ability to select which plots are to be part of the final report is also available. For final report, an option to report only the alcohol events that meet the set requirements of MIN_PEAK_DURATION, MIN_PEAK_RISE_SLOPE, and MIN_

PEAK_FALL_SLOPE is available. A similar option to report only the tamper events that meet the set requirements is available.

The device detects transdermal alcohol content through custom sensors. The custom sensors react to epidermal ethanol concentrations and record a current change which is converted to a voltage value and transmitted via Bluetooth. For field operation, the read output in Volts needs to be converted to the underlying ethanol and hence, transdermal alcohol content (TAC). To accomplish this, it is necessary that the change in voltage (current) from the custom sensor should only reflect changes in alcohol level from epidermal emission of ethanol. Therefore, changes in voltage (current) resulting from other factors, such as humidity/temperature fluctuations, or variation in sensor to sensor, needs to be removed.

With reference to FIG. 28 flowchart, this can be accomplished using "Correction/Conversion Factors" as discussed above.

For the procedures described herein, the hardware and software requirements are noted below according to one or more embodiments.

Hardware: 1) Device disclosed herein; 2) USB Programmer Unit: This programmer unit includes the ATMEL-ICE programmer and USB cables with a micro-USB which can connect to the USB on the device. The programmer unit is needed to flash the Firmware onto the unit. 3) Laptop/Computer: The GUI software package runs on the laptop/computer. Smartphone: For App operation. Currently, an Android app is used; however, the same can be easily adopted to an iPhone.

Software: 1) GUI: This is a software package which allows programming and initialization of the device. 2) Custom App: This is a custom app which uses Bluetooth to program the unit for field operation and record data from the device.

The device is factory programmed with firmware and assigned a unit name typically containing the last 4 digits of the MAC address of the Bluetooth chip on board. The Firmware is the system software coded onto the microcontroller chip and controls the operation of the electronics.

The first step in setting up the device for field installation is assigning an ID to the device. In this step, the GUI software is used to interact with the device and assign a unique ID which will be used to pair the hardware unit to one phone. The ID (along with the Bluetooth MAC address) can also be used as a wearer ID to manage multiple units in the field.

A) Connect Device to Computer: Plug in the USB programmer cable to the device and the other end (two USBs) to the administrator laptop/desktop.

Figure 29A:
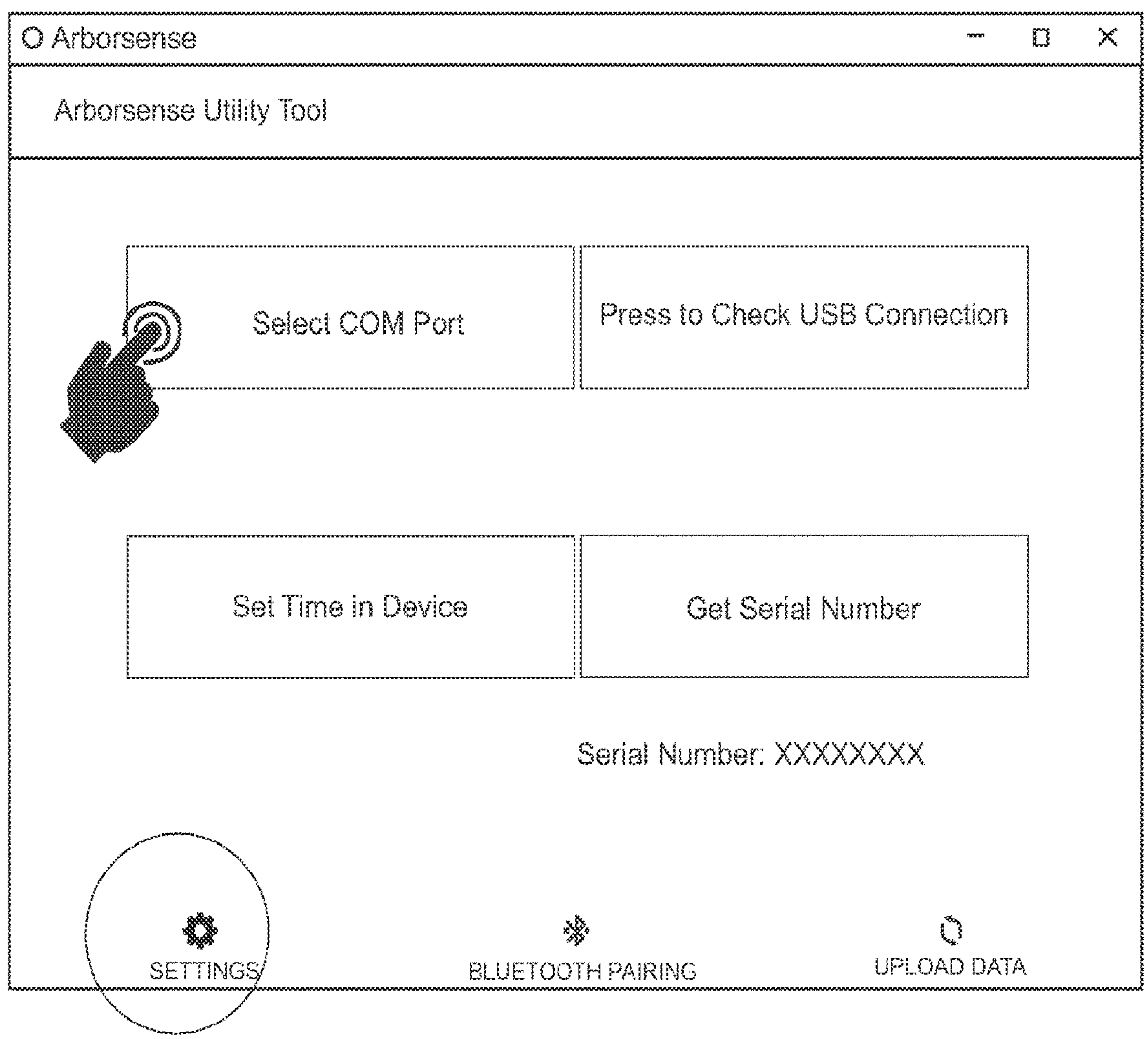
FIGS. 29A and 29B illustrate a graphical user interface for establishing a COM port connection with the device according to one or more embodiments.
Figure 29B:
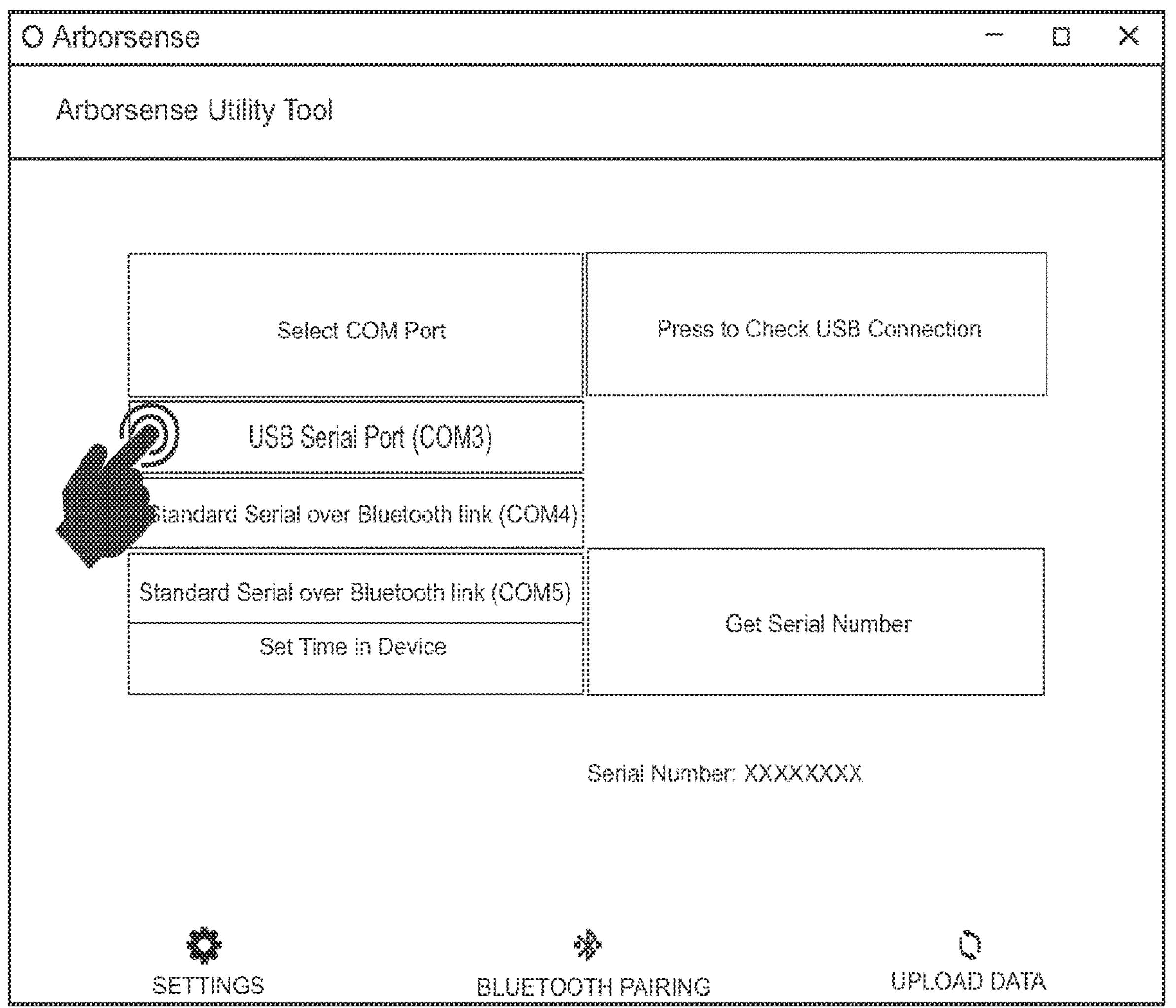

B) Establish COM Port Connection: Open the GUI in the 'Settings' window (FIG. 29) and select the USB Serial COM port in the drop-down menu to connect to the hardware unit. From the GUI, we can select "Set Time in Device" to hardcode the time onto the device also. "Set Time" can also be done through the Custom app, as described below. The GUI settings page can be used to Get Serial Number to confirm the hardware ID of the module. The Serial Number is populated at the bottom of the page.

Figure 30:
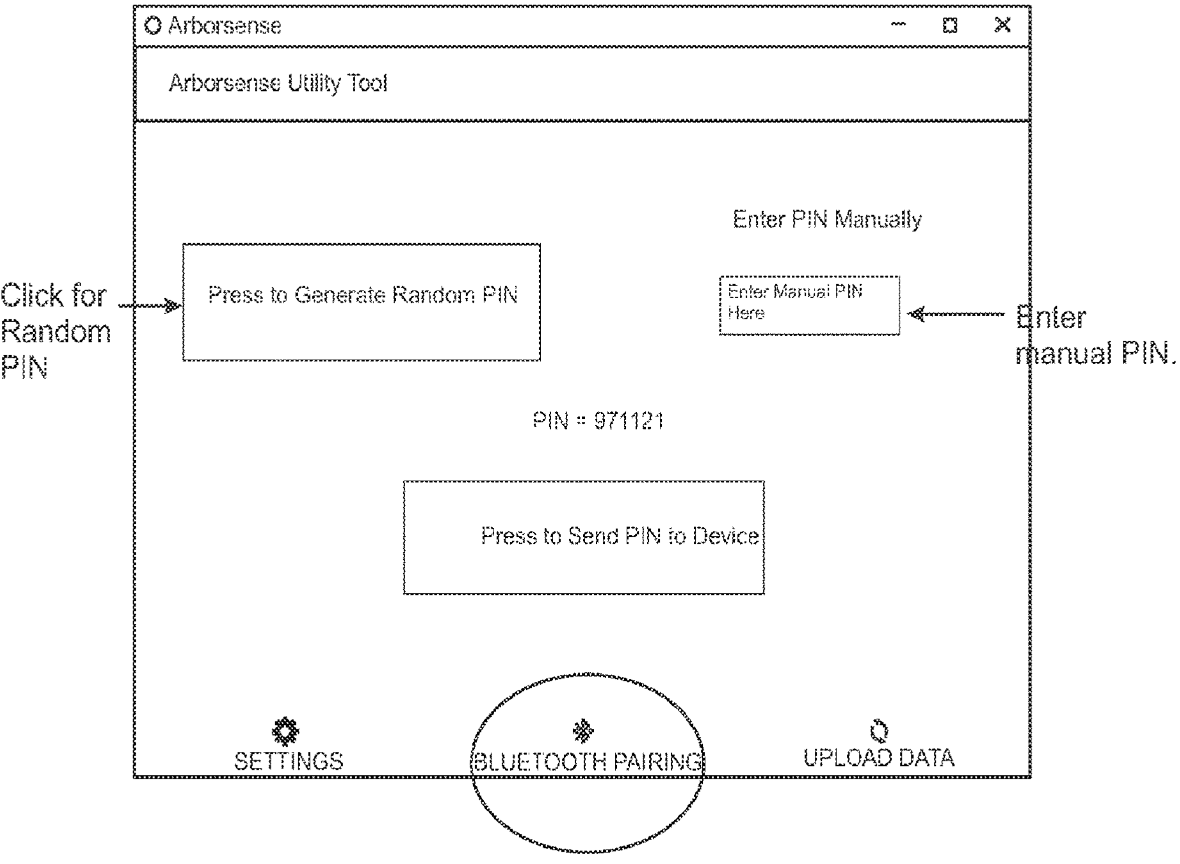
FIG. 30 illustrates a graphical user interface for generating and assigning a unique ID to the device according to one or more embodiments.

C) Generate and Assign ID: Switch to the "Bluetooth Pairing" window to generate and assign a unique PIN/ID to the device (FIG. 30). PIN/ID can be generated via a random number generator or manually entered. Assign the PIN to the unit by pressing the Press to Send PIN to device button. Later, the phone may be bonded and paired to the device with this unique ID through the Android app and, once paired and bonded, the device will only communicate with that phone.

The unit has now been assigned a unique ID and is ready to be programmed for wearer installation.

Figure 31:
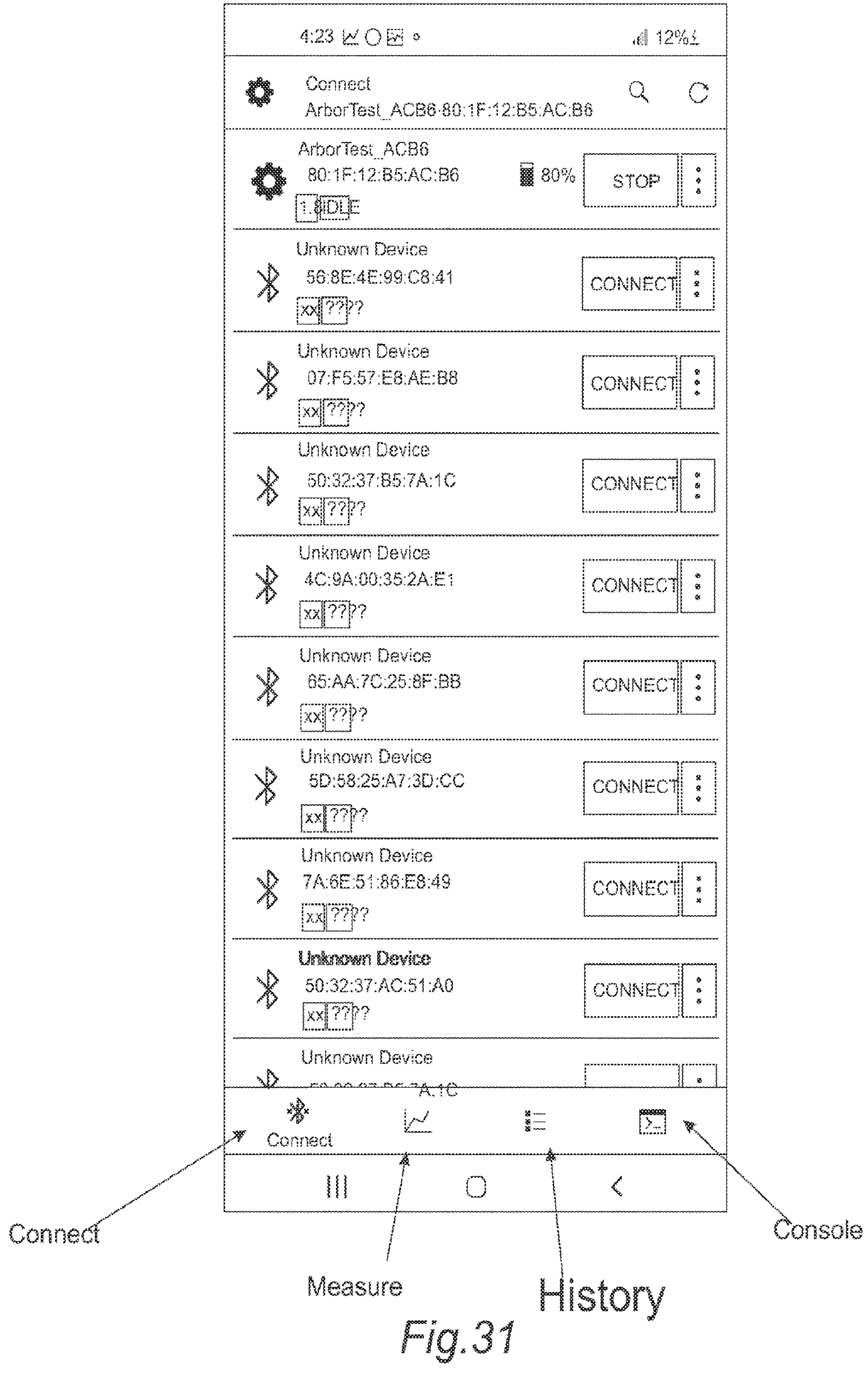
FIG. 31 illustrates a graphical user interface of an app for use with the device according to one or more embodiments.

The custom app may be used with an android phone. In other implementations, an iPhone version of the same app may be used as well. With reference to FIG. 31, in one or more embodiments, the general layout of the app may include four windows as described below.

WINDOW 1: CONNECT. The app opens with the 'CONNECT' window up front. This window shows all the available Bluetooth devices in the vicinity of the phone. The following operations can be performed in this window: a) Establish a Bluetooth connection with the device; b) Bond and Pair with the device; c) Enter programming mode for a particular device. Programming mode allows sending commands to the hardware unit to: i. Turn the custom graphene sensor on/off; ii. Turn Powerdown mode on/off; iii. Set Record mode operation; iv. Set Gain Resistor value; v. Set the time on the unit; vi. Perform a flash memory read; vii. Set the timer for Livestream mode; viii. Start Livestream mode.

Figure 32:
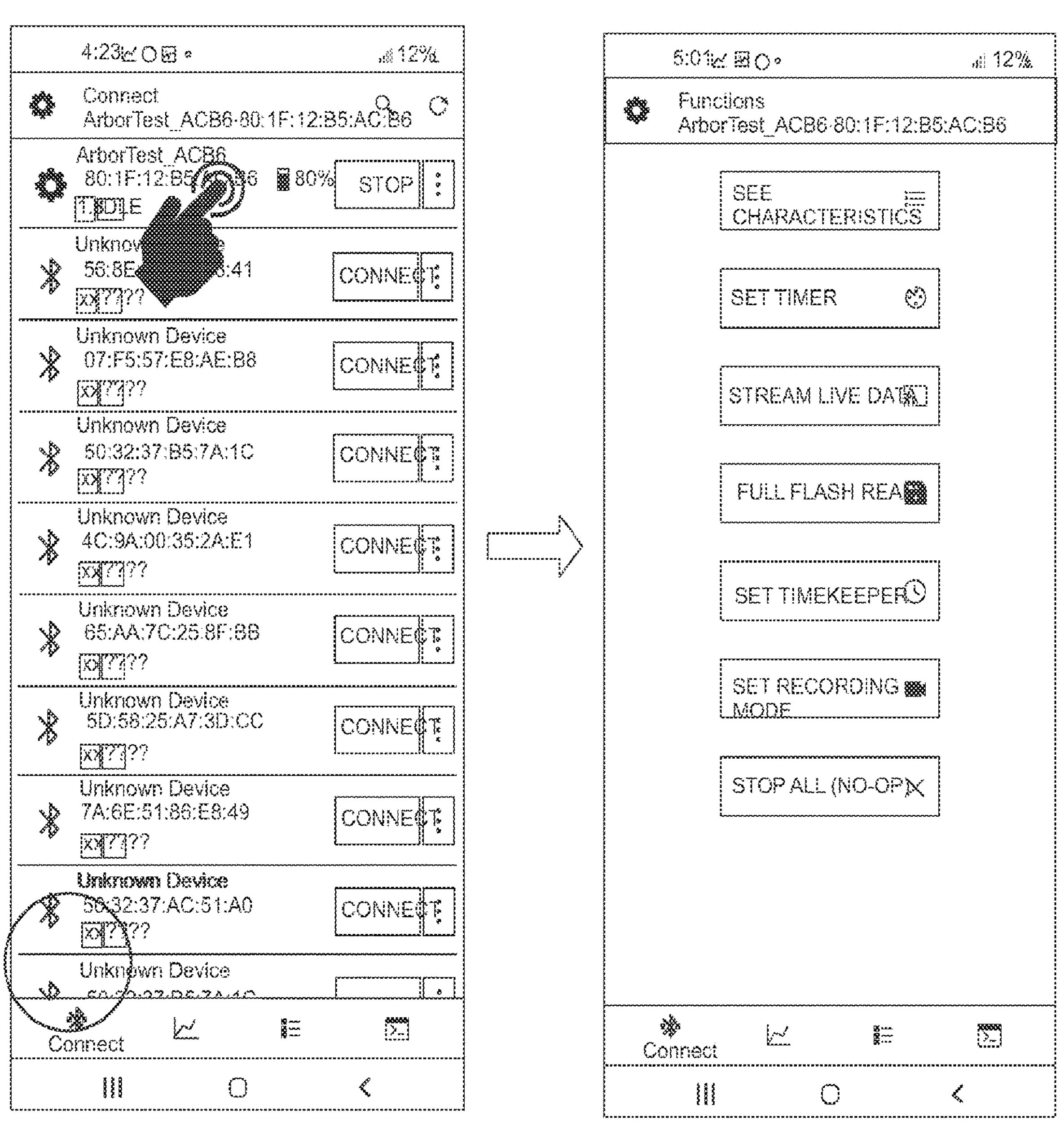
FIG. 32 illustrates setting characteristics in the app according to one or more embodiments.

With reference to FIG. 32, many of these functions can be performed through tabs available on the panel while some of these require entering the 'SET CHARACTERISTIC' tab to send command codes in HEX format.

Figure 33:
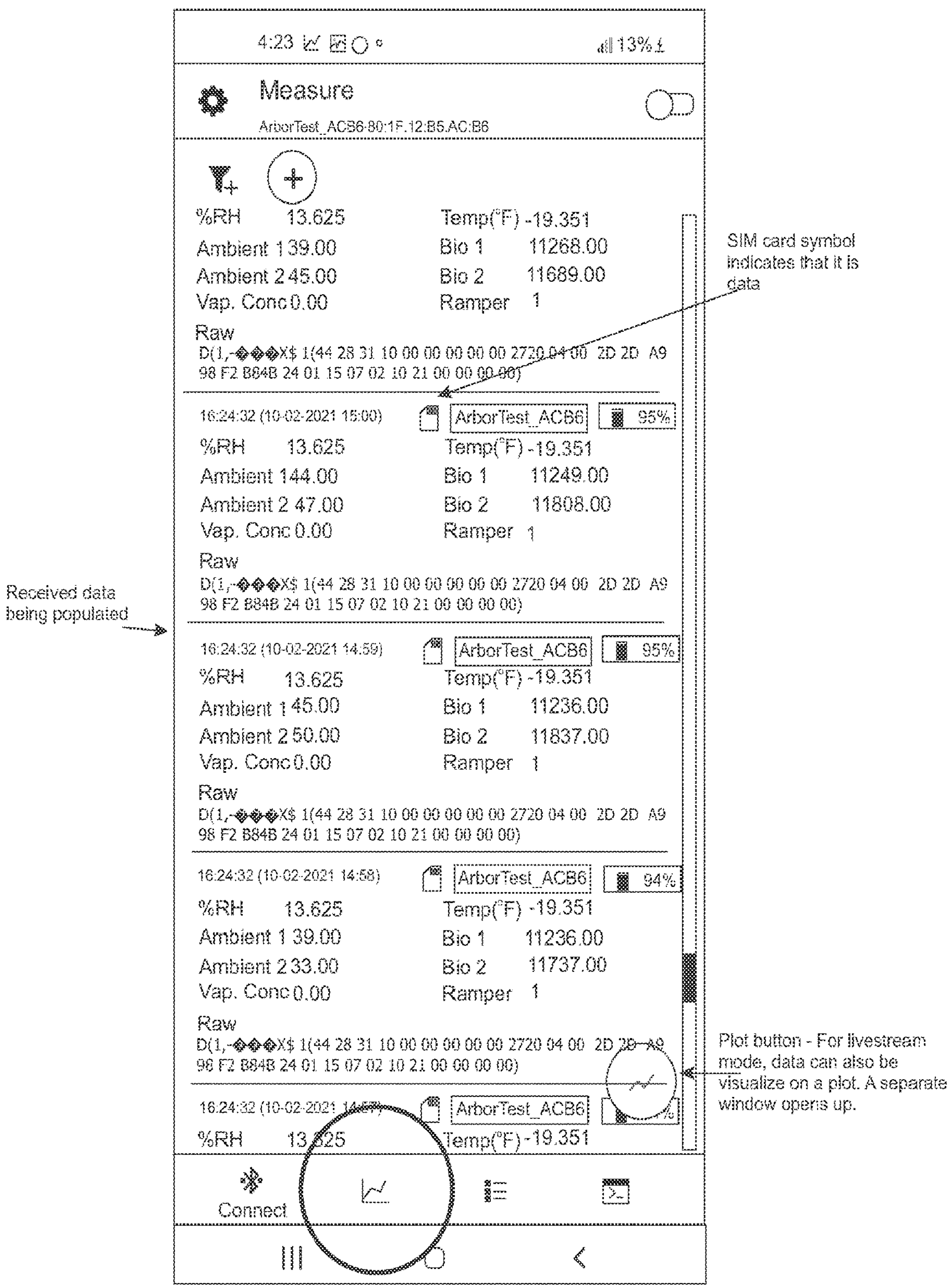
FIG. 33 illustrates a measure window of the app which presents data being received by the phone from the hardware unit according to one or more embodiments.
Figure 34:
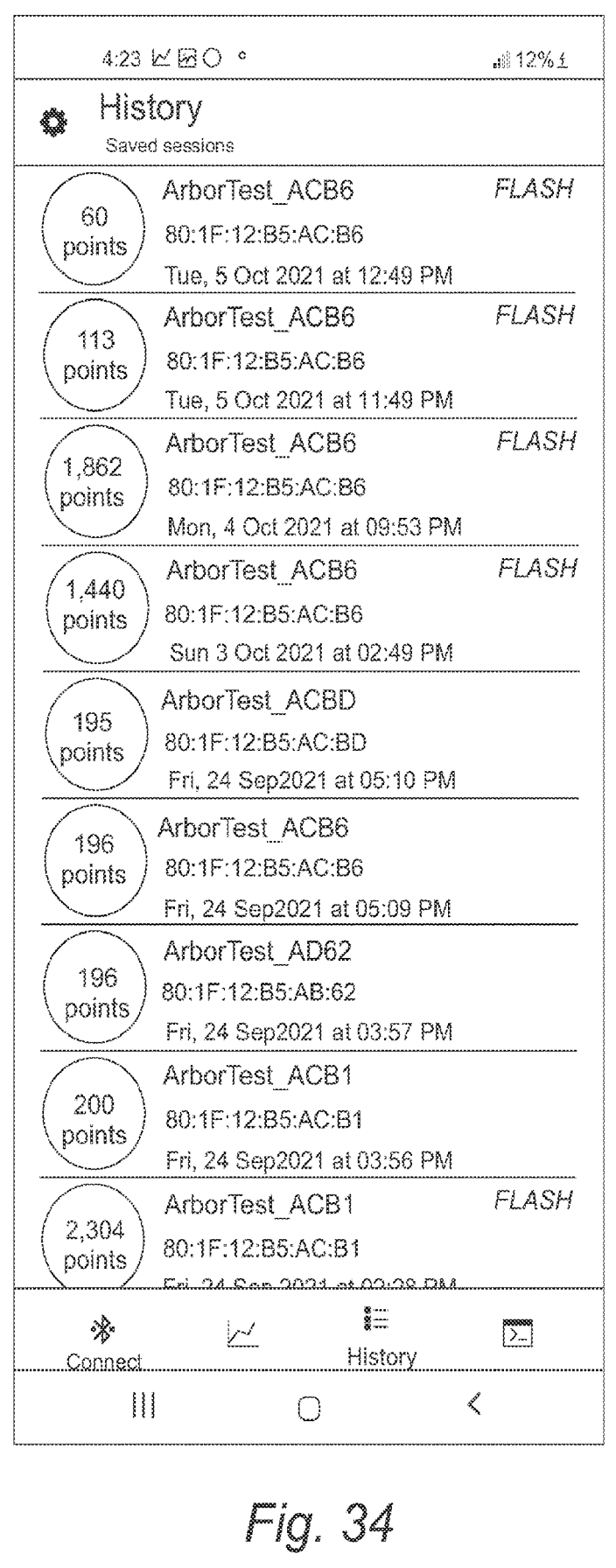

WINDOW 2: MEASURE. The Measure window (FIG. 33) is active only when a Bluetooth connection is established and active. The Measure window presents the data being received by phone from the hardware unit whether it is livestream data in real-time or Flash Data WINDOW 3: HISTORY. The history window (FIG. 34) shows the data files received by the hardware unit stored by the app in the phone memory. For Flash data, the file is denoted by a FLASH mark. All other files are Livestream mode files. History files denote the device name, number of points, Bluetooth MAC address, and date and time when they were stored.

Figure 35:
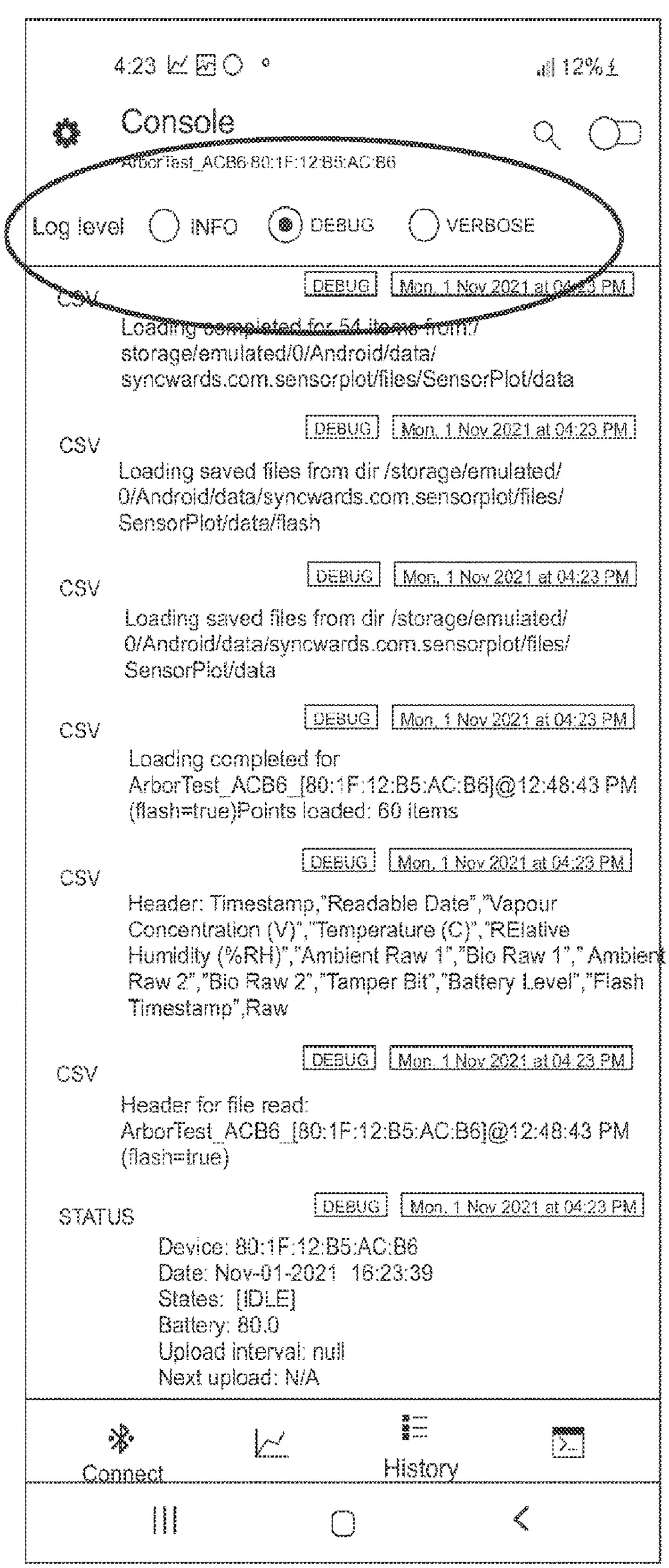
FIG. 35 illustrates a console window of the app for preserving all the logs related to the app performance according to one or more embodiments.

WINDOW 4: CONSOLE. The Console window (FIG. 35), also known as the log window, preserves all the logs related to the app performance. All actions performed by the app with their timestamp are documented in the logs and saved on the phone in a log folder. The log files provide important information in case of errors or troubleshooting.

APP OPERATION TO SETUP DEVICE FOR FIELD INSTALLATION. In this step, the app is used to send operational commands to the Hardware unit via Bluetooth to initialize it for field installation.

A. Connect Device to app: In the "Connect" window, select the device name assigned in the Firmware and press CONNECT.

Figure 36:
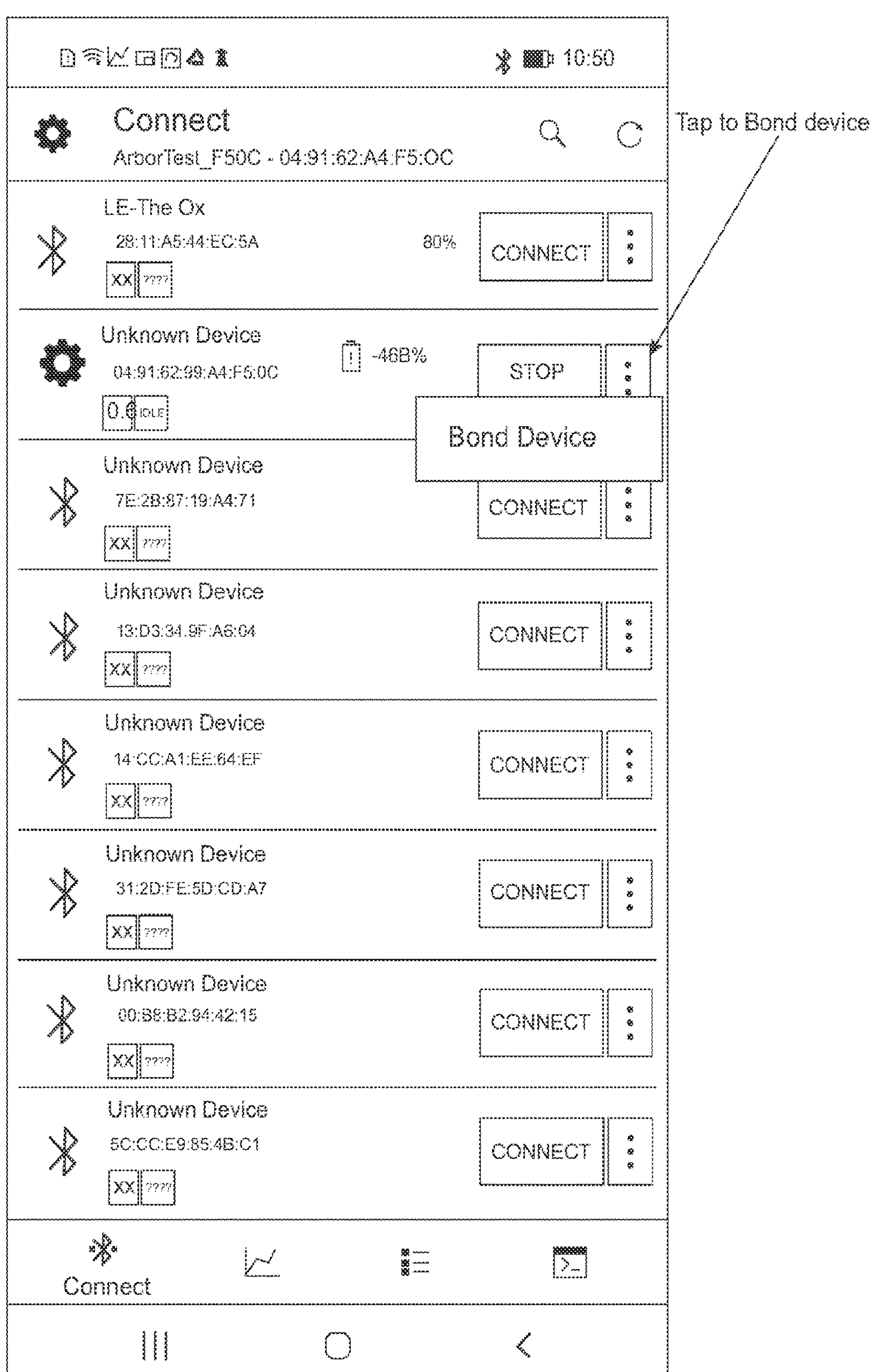
FIG. 36 illustrates bonding and pairing the device to the phone according to one or more embodiments.

B. Bond and pair device to the phone (FIG. 36): Tap on the menu and select Bond Device. At this step, the app will ask for the PIN for pairing the phone with the hardware unit. Use the PIN/ID that was assigned to the unit as described above.

Figure 37:
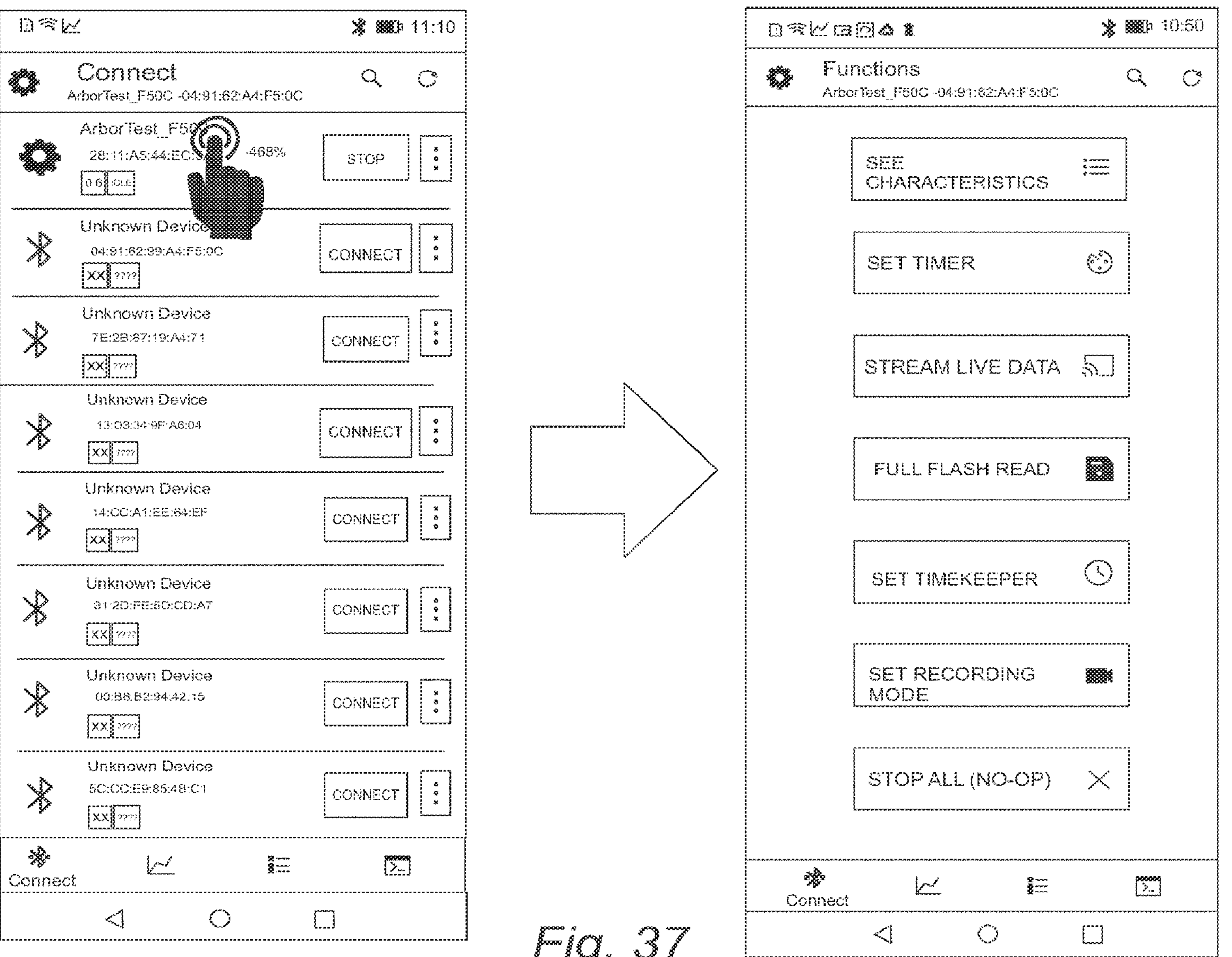
FIG. 37 illustrates programming the device for field use according to one or more embodiments.
Figure 38:
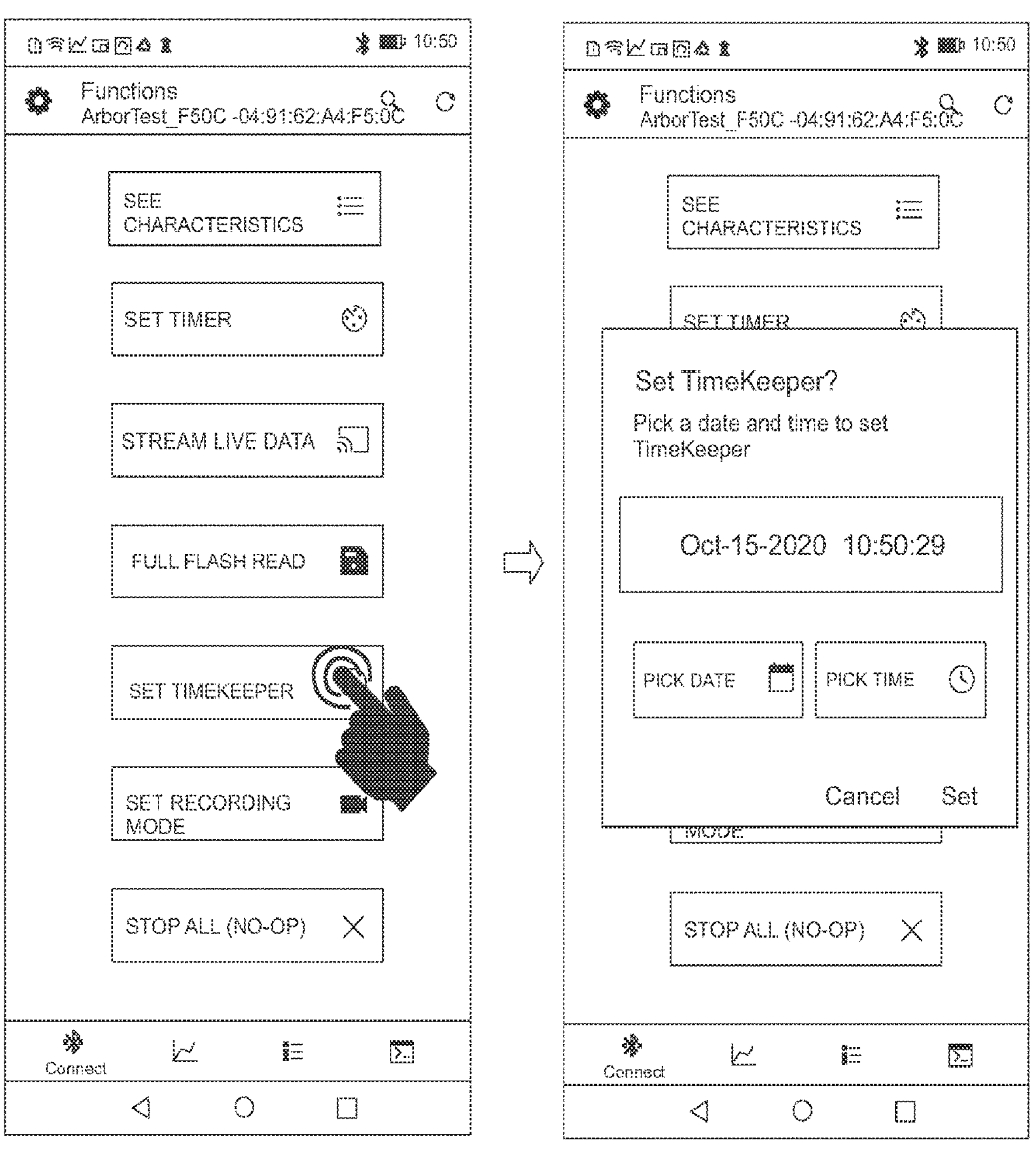
FIG. 38 illustrates setting the date and time for the device via the app according to one or more embodiments.
Figure 39:
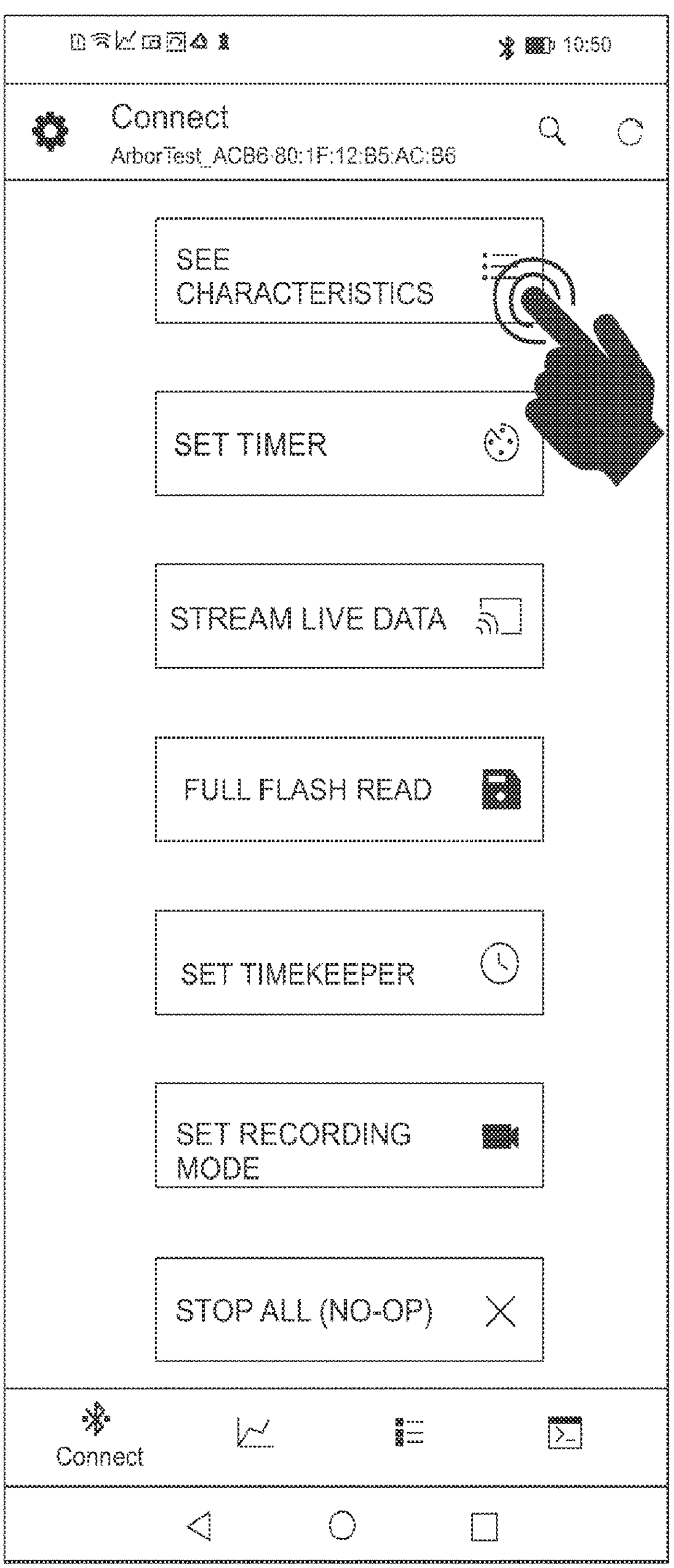
FIG. 39 illustrates using the set characteristic tab for turning the device custom sensor on or entering power down mode via the app according to one or more embodiments.
Figure 40:
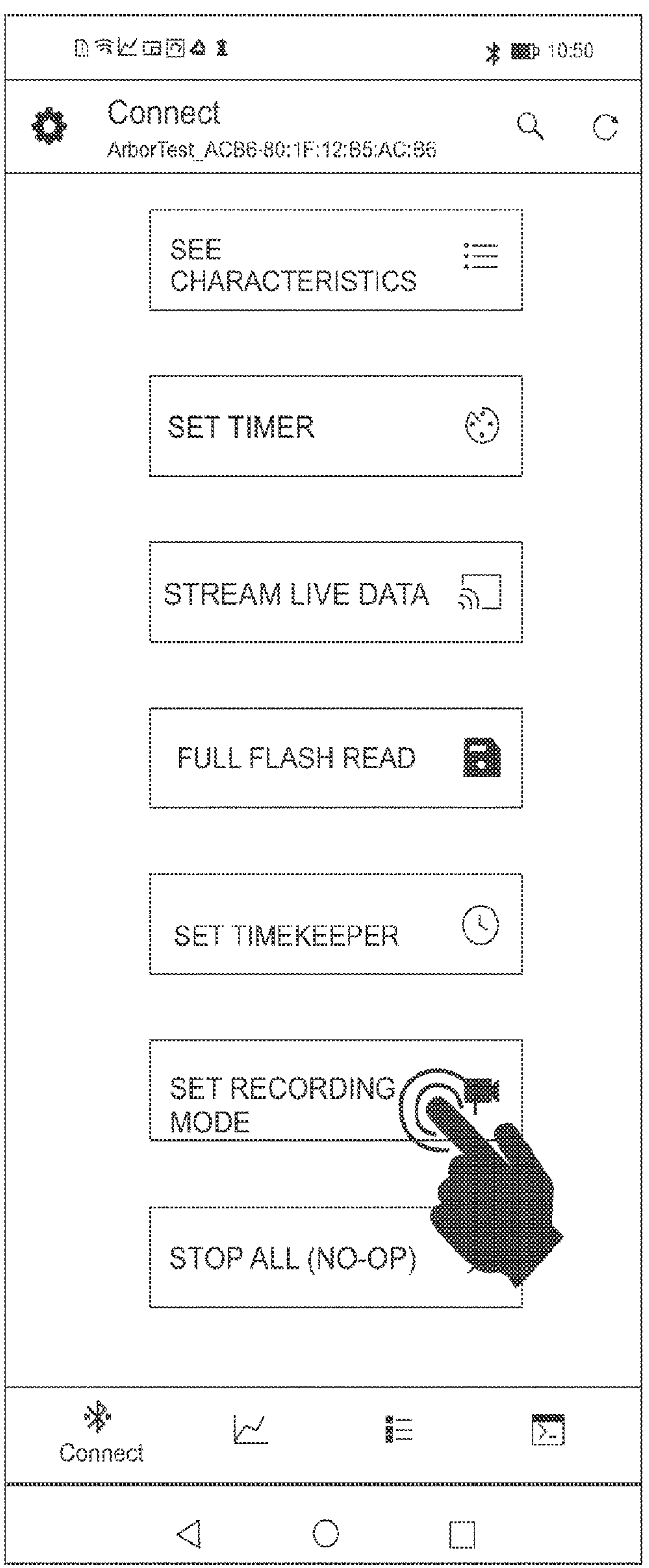
FIG. 40 illustrates setting a recording mode with the app according to one or more embodiments.
Figure 41:
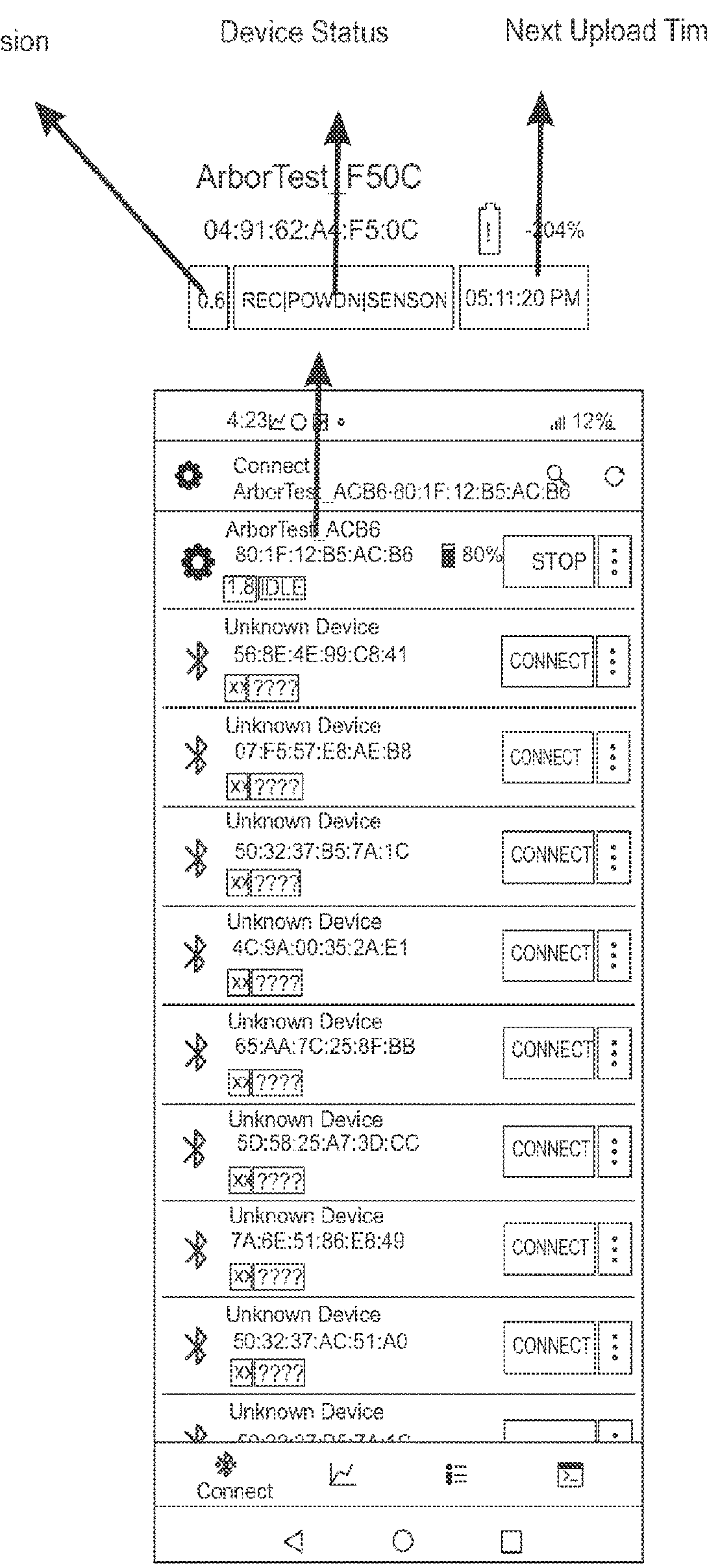
FIG. 41 illustrates confirming the status of the device on the app according to one or more embodiments.

C. Program the device for field use (FIG. 37): Tap on the device name. This will open the Programming/Functions mode. This mode is used to program or send commands to the device. i. Set Timekeeper (FIG. 38): Tap on SET TIMEKEEPER and set the date and time. Current date/time is auto-populated. Press SET to select. ii. Turn Sensor ON (FIG. 39): Tap Set Characteristic function in the functions window. This opens the GATT services window. Under the UART Measurement Service drop down menu, select Client Data In. Enter the sensor on HEX command in the pop-up window and hit SEND to turn sensor ON. iii. Initiate Power Down Mode: In the same set characteristics functions window SEND the powerdown HEX command to initiate PowerDown mode. iv. Set Recording Mode (FIG. 40): Tap on Set Recording Mode to set the parameters for data collection. Set DAQ measuring time. This represents how often data from all sensors on the hardware unit is collected by the microcontroller. Set BLE Upload frequency. This represents how often the unit uploads the collected data to the phone. This setting also sets the internal timer for the app to wake up and scan for the active BLE device. Set BLE Upload timeout. This represents how long the phone will look for a Bluetooth connection from the unit at the time of 'BLE Upload' before timing out. Confirm the status of the device on the app by going back to the 'Connect Window' (FIG. 41). The status should read REC|POWDN|SENSON. The tray also shows the next 'BLE Upload time'. Once the REC mode is setup, the hardware unit and phone app synchronize their timers to ensure that the phone wakes up around the BLE upload time to connect to the unit v. Disconnect the app: Hit 'STOP' to disconnect from the app.

D. Close all connections. Disconnect the USB from the device to send the unit into Powerdown mode. The device is ready to be installed on a wearer.

In another aspect, the app operation includes multiple steps and is built this way to provide flexibility research, iterate, and troubleshoot. The sequence of steps can be greatly reduced. For example, SET TIME >SENSOR ON>POWER DOWN>RECORD steps can be combined into one step in another embodiment.

ADVERTISEMENT MODE OPERATION. Once the unit has been set up for field operation, it is in the lowest power consumption state. The unit can only be taken off by cutting the wrist strap.

Figure 42:
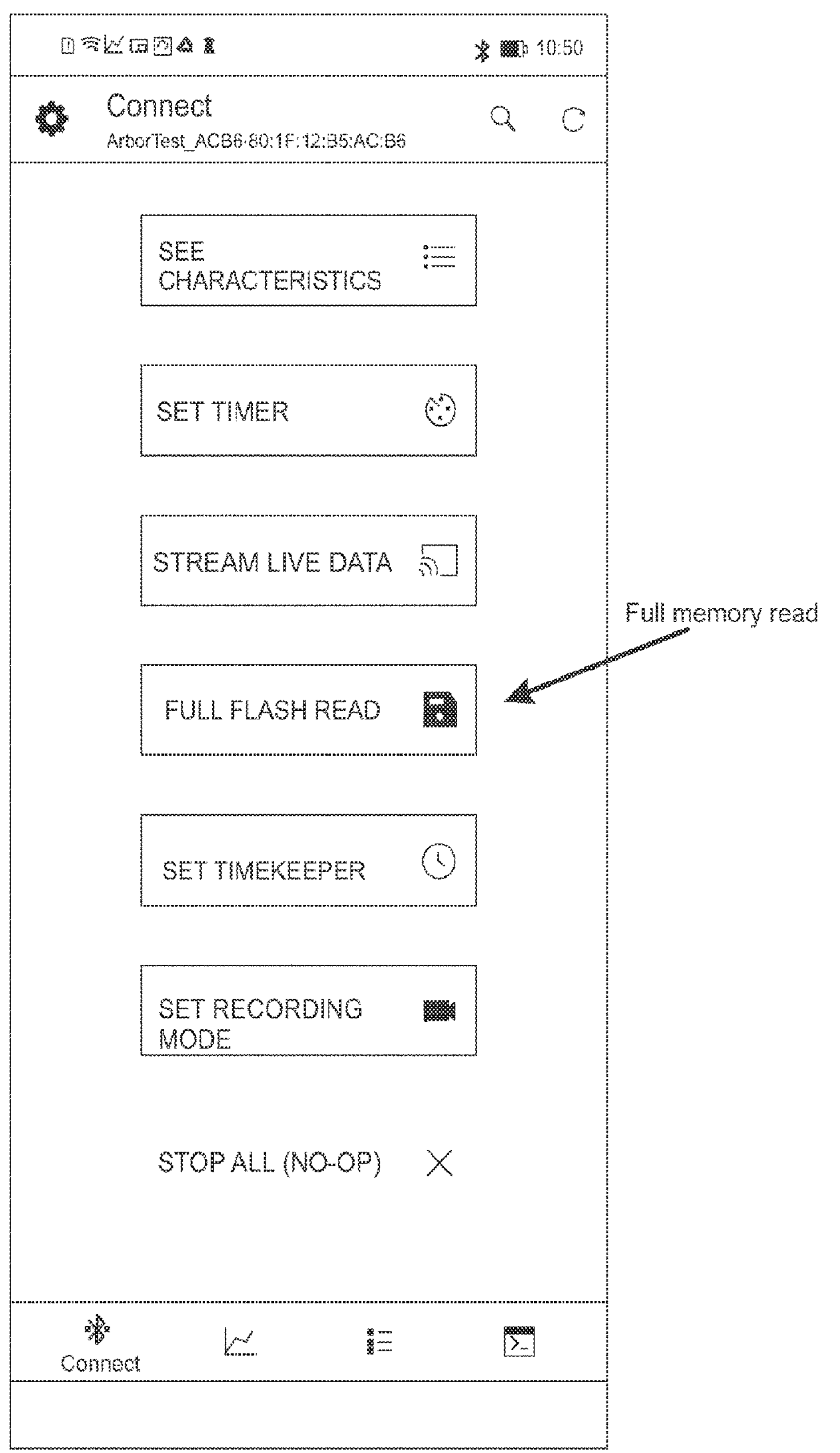
FIG. 42 illustrates reading the full flash memory via the app during an advertisement mode of the device according to one or more embodiments.

There may be occasions where an administrator would want to interact with the device in the field without taking it off the wearer's wrist. This is possible in the ADV mode. In one or more embodiments, the ADV mode takes place every nth minute from the start of the REC mode and times out after a set time period. These parameters can be set by the administrator. Within this time window during the ADV Mode connection can be established with the device through the app. The Programming/Functions Mode can be accessed to perform diagnostics (FIG. 42). e.g., for a. Re-sync the unit b. Do a Full EEPROM READ to collect the entire data.

Bluetooth Commands and Notifications. The Bluetooth commands can be sent to the hardware unit the SET CHARACTERISTIC panel and or implemented through a button that can be tapped in the FUNCTIONS window.

For each command sent, the app gets back a notification response from the Hardware unit. If a notification is not received, it indicates that the operation was not performed. All of this information is also accessible through the log files created in the app. In one or more embodiments, the notifications include: Version Command) Notification; Error Command Notification; Sensor ON/OFF Notification; Livestream Notification; Livestream Timer Notification; Flash memory read Notification; Record mode Notification; Advertisement Mode Notification; Powerdown Mode Notification; Timekeeper chip Notification; and Flash Erase Notification.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A wrist-worn device for monitoring alcohol consumption, the wrist-worn device comprising:

a device housing comprising:

an upper housing;

a lower housing having a top wall and a circumferential side wall, the top wall defining a first access opening, the lower housing attached to the upper housing; and a wrist piece having a first face and a second face, the wrist piece defining a trench in the first face that protrudes from the second face as a closed curve-shaped protrusion, the closed curve-shaped protrusion configured to fit on a subject's wrist surface such that the closed curve-shaped protrusion presses into a subject's skin to form a liquid and vapor seal inhibiting transdermally emitted ethanol from escaping outside a collection area, the lower housing and the wrist piece cooperatively forming an amplification chamber, the amplification chamber being a cavity below the top wall of the lower housing and above the wrist piece, wherein the wrist piece defines a plurality of vent holes that allow transdermally emitted ethanol to enter the amplification chamber;

an electrochemical sensor for ethanol having an electrode aligning to the first access opening;

control circuitry enclosed in the upper housing, the control circuitry configured to receive measurements from the electrochemical sensor and to calculate transdermal alcohol concentration; and a water-absorbing material sequestered in the amplification chamber, including in the trench.

2. The wrist-worn device of claim 1, wherein the control circuitry includes a microprocessor.

3. The wrist-worn device of claim 1, wherein the control circuitry is configured to communicate with a computing device.

4. The wrist-worn device of claim 3, wherein the computing device is a smartphone, tablet, or a computer.

5. The wrist-worn device of claim 3, wherein the computing device and/or the control circuitry is configured to receive a plurality of alcohol measurements as a function of time over a first predetermined time interval to provide a time-dependent alcohol concentration plot.

6. The wrist-worn device of claim 5, wherein the computing device and/or the control circuitry is configured apply a baseline correction algorithm to the time-dependent alcohol concentration plot to determine a baseline.

7. The wrist-worn device of claim 6, wherein the baseline correction algorithm is a rubberband correction algorithm.

8. The wrist-worn device of claim 5, wherein the computing device and/or the control circuitry is configured to apply a humidity correction factor and a temperature correction factor.

9. The wrist-worn device of claim 5, wherein the computing device and/or the control circuitry is configured to evaluate peaks in the time-dependent alcohol concentration plot by determining a first slope for a rise in alcohol concentration and a second slope for an associate fall in alcohol concentration.

10. The wrist-worn device of claim 9, wherein the computing device and/or the control circuitry is configured to determine that a peak in the time-dependent alcohol concentration plot is positive for alcohol consumption if the peak extends from the baseline by a predetermined amount and if the first slope and the second slope are less than a predetermined rising slope and a predetermined falling slope, respectively.

11. The wrist-worn device of claim 1 further comprising a tamper-resistant wristband attached to the device housing.

12. The wrist-worn device of claim 1 wherein the upper housing defines a first vent conduit in fluid communication with the first access opening, the first vent conduit configured for removing water vapor and other vapors from the amplification chamber through a first vent opening.

13. The wrist-worn device of claim 12, wherein the upper housing defines a second vent conduit configured for providing air flow or oxygen flow to the electrochemical sensor in a space above the upper housing.

14. The wrist-worn device of claim 13 further comprising a first steam guard at the first vent opening and a second steam guard at the second vent opening, the first steam guard and the second steam guard preventing the inflow of liquid water.

15. The wrist-worn device of claim 14 wherein the first steam guard and the second steam guard each independently include multiple layers of pyrolytic graphite or a compressed metal foam.

16. The wrist-worn device of claim 1 further comprising one or more tamper sensors.

17. The wrist-worn device of claim 16, wherein the one or more tamper sensors are selected from the group consisting of IR sensors, ambient sensors, humidity sensors, temperature sensors, a tamper bit, and combinations thereof.

18. The wrist-worn device of claim 17, wherein the one or more tamper sensors is an IR sensor mounted in the control circuitry.

19. The wrist-worn device of claim 18 further comprising an IR transparent rod in optical communication with the IR sensor and the first face of the wrist piece.

20. The wrist-worn device of claim 17, wherein the computing device and/or the control circuitry is configured to determine that the time-dependent tamper sensor value is positive for tamper if the signal changes from the baseline by a predetermined amount and for a particular duration.

21. The wrist-worn device of claim 1, wherein the water-absorbing material is a super absorbent polymer.

22. The wrist-worn device of claim 21, wherein the super absorbent polymer is sodium polyacrylate.

23. The wrist-worn device of claim 1 configured to be continuously worn for at least 30 days if not submersed in water.

24. An alcohol monitoring system including the wrist-worn device of claim 1.

* * * * *